(12) United States Patent
Tullis et al.

(10) Patent No.: US 8,852,182 B2
(45) Date of Patent: Oct. 7, 2014

(54) ELECTRODE ASSEMBLY WITH SEPARATE BIPOLAR CANNULA AND SUPPLY ELECTRODE

(75) Inventors: Philip James Tullis, Kalamazoo, MI (US); Chamara Gamhewage, Portage, MI (US); Douglas Alan Staunton, Kalamazoo, MI (US); Eland Cramlet, Portage, MI (US); Nicole Fickes, Mattawan, MI (US); Andy Staats, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 375 days.

(21) Appl. No.: 13/042,670

(22) Filed: Mar. 8, 2011

(65) Prior Publication Data

US 2011/0160723 A1 Jun. 30, 2011

Related U.S. Application Data

(62) Division of application No. 11/381,064, filed on May 1, 2006, now Pat. No. 7,918,852.

(60) Provisional application No. 60/676,092, filed on Apr. 29, 2005.

(51) Int. Cl.
  *A61B 18/14* (2006.01)
  *A61B 17/00* (2006.01)
  *A61B 18/00* (2006.01)

(52) U.S. Cl.
  CPC ... *A61B 18/1477* (2013.01); *A61B 2017/00867* (2013.01); *C08L 2201/12* (2013.01); *A61B 2018/00434* (2013.01); *A61B 2018/00821* (2013.01); *A61B 2018/0044* (2013.01); *A61B 2017/00212* (2013.01)
  USPC .............................................. 606/41; 606/48

(58) Field of Classification Search
  USPC ...................................................... 606/48–50
  See application file for complete search history.

(56) References Cited

U.S. PATENT DOCUMENTS 3,946,738 A 3/1976 Newton et al.
3,964,487 A 6/1976 Judson
(Continued)

FOREIGN PATENT DOCUMENTS

DE 2926744 1/1981
DE 3838840 5/1990
DE 3930451 3/1991

OTHER PUBLICATIONS

International Search Report and Written Opinion dated Jan. 17, 2007; International Application No. PCT/US2006/016731; International Filing Date Jan. 5, 2006.

(Continued)

*Primary Examiner* — Jaymi Della
(74) *Attorney, Agent, or Firm* — Howard & Howard Attorneys PLLC

(57) ABSTRACT

An electrosurgical system preferably used for denervation procedures of nerve tissue has a control unit and a pluggable electrode assembly. The electrode assembly has a disposable cannula and a preservable supply electrode assembly. The cannula has a tubular body that projects axially from a pointed distal end for piercing tissue to a proximal end engaged to a first coupling assembly of the cannula. The supply electrode assembly has a second coupling assembly and a supply electrode that projects axially and removably into a through-bore of the body when in an operating state. The first and second coupling assemblies are configured to releasably interlock to prevent clockwise and counterclockwise rotation of the supply electrode in the body.

19 Claims, 14 Drawing Sheets

(56) References Cited

U.S. PATENT DOCUMENTS

| | | | |
|---|---|---|---|
| 3,980,085 | A | 9/1976 | Ikuno |
| 4,003,380 | A | 1/1977 | Wien |
| 4,043,342 | A | 8/1977 | Morrison, Jr. |
| 4,116,198 | A | 9/1978 | Roos |
| 4,126,137 | A | 11/1978 | Archibald |
| 4,188,927 | A | 2/1980 | Harris |
| 4,214,804 | A | 7/1980 | Little |
| 4,245,649 | A | 1/1981 | Schmidt-Anderson |
| 4,474,179 | A | 10/1984 | Koch |
| 4,476,862 | A | 10/1984 | Pao |
| 4,483,338 | A | 11/1984 | Bloom et al. |
| 4,565,200 | A | 1/1986 | Cosman |
| 4,590,934 | A | 5/1986 | Malis et al. |
| 4,651,734 | A | 3/1987 | Doss et al. |
| 4,655,226 | A | 4/1987 | Lee |
| 4,674,499 | A | 6/1987 | Pao |
| 4,685,459 | A | 8/1987 | Koch et al. |
| 4,727,874 | A | 3/1988 | Bowers et al. |
| 4,844,063 | A | 7/1989 | Clark |
| 4,907,585 | A | 3/1990 | Schachaf |
| 4,907,589 | A | 3/1990 | Cosman |
| 4,955,377 | A | 9/1990 | Lennox et al. |
| 4,966,597 | A | 10/1990 | Cosman |
| 5,007,908 | A | 4/1991 | Rydell |
| 5,009,656 | A | 4/1991 | Reimels |
| 5,019,076 | A | 5/1991 | Yamanashi et al. |
| 5,267,997 | A | 12/1993 | Farin et al. |
| 5,342,357 | A | 8/1994 | Nardella |
| 5,364,395 | A * | 11/1994 | West, Jr. .................... 606/46 |
| 5,383,874 | A | 1/1995 | Jackson et al. |
| 5,403,311 | A | 4/1995 | Abele et al. |
| 5,433,739 | A | 7/1995 | Siuijer et al. |
| 5,458,597 | A * | 10/1995 | Edwards et al. .............. 606/41 |
| 5,651,780 | A | 7/1997 | Jackson et al. |
| 5,697,281 | A | 12/1997 | Eggers et al. |
| 5,697,536 | A | 12/1997 | Eggers et al. |
| 5,697,882 | A | 12/1997 | Eggers et al. |
| 5,697,909 | A | 12/1997 | Eggers et al. |
| 5,827,280 | A | 10/1998 | Sandock et al. |
| 5,843,019 | A | 12/1998 | Eggers et al. |
| 5,888,198 | A | 3/1999 | Eggers et al. |
| 5,891,095 | A | 4/1999 | Eggers et al. |
| 5,902,272 | A | 5/1999 | Eggers et al. |
| 6,004,319 | A | 12/1999 | Goble et al. |
| 6,056,746 | A | 5/2000 | Goble et al. |
| 6,066,134 | A | 5/2000 | Eggers et al. |
| 6,106,524 | A | 8/2000 | Eggers et al. |
| 6,146,380 | A | 11/2000 | Racz et al. |
| 6,149,620 | A | 11/2000 | Baker et al. |
| 6,159,194 | A | 12/2000 | Eggers et al. |
| 6,193,715 | B1 * | 2/2001 | Wrublewski et al. .......... 606/45 |
| 6,312,408 | B1 | 11/2001 | Eggers et al. |
| 6,312,428 | B1 | 11/2001 | Eggers et al. |
| 6,379,350 | B1 | 4/2002 | Sharkey et al. |
| 6,416,508 | B1 | 7/2002 | Eggers et al. |
| 6,506,189 | B1 | 1/2003 | Rittman, III et al. |
| 6,582,441 | B1 | 6/2003 | He et al. |
| 6,632,220 | B1 | 10/2003 | Eggers et al. |
| 6,837,884 | B2 | 1/2005 | Woloszko |
| 7,150,747 | B1 * | 12/2006 | McDonald et al. ............ 606/45 |
| 2002/0019596 | A1 | 2/2002 | Eggers et al. |
| 2002/0065541 | A1 | 5/2002 | Fredricks et al. |
| 2004/0116793 | A1 | 6/2004 | Taimisto et al. |

OTHER PUBLICATIONS

European Search Report for Application No. EP 10001841, dated Mar. 22, 2010, 2 pages.

F.L. Fischer, "Neuro N50 HF-Koagulator" Product Brochure, Oct. 1987, 7 pages.

Spark Erosion, "Vaporization of Atherosclerotic Plaques", Jun. 1983, 5 pages.

* cited by examiner

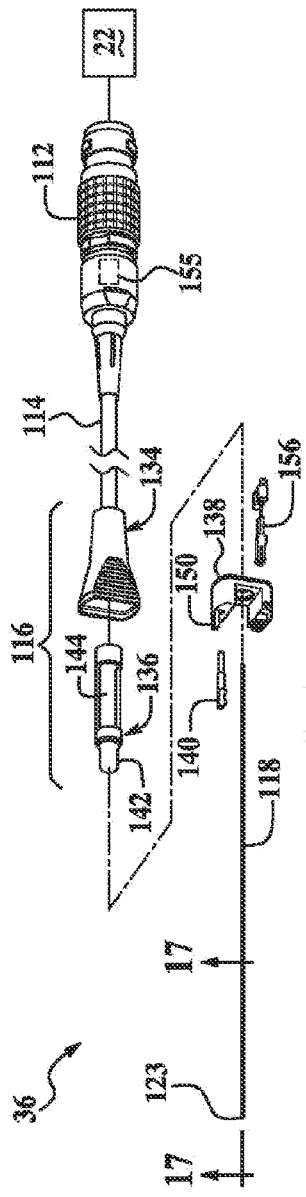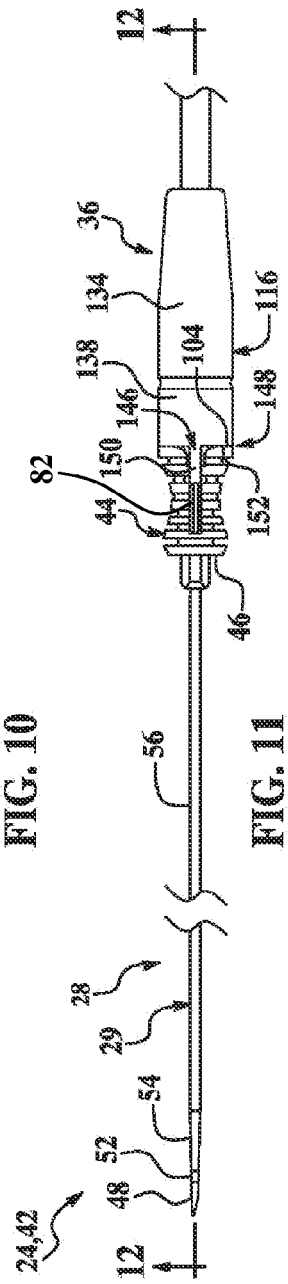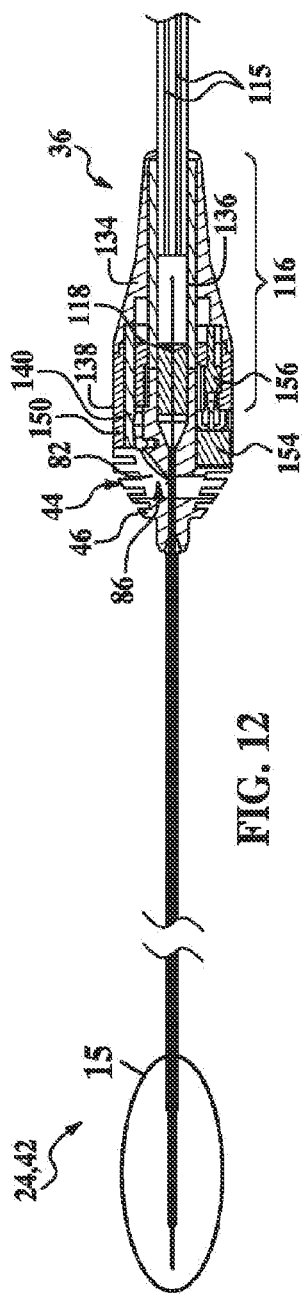
FIG. 10
FIG. 11
FIG. 12

| | |
|---|---|
| NAME | ～170 |
| PART No. | ～172 |
| REV | ～174 |
| SERIAL No. | ～176 |
| MANUFACTURER | ～178 |
| MIN SOFTWARE REV | ～182 |
| MIN HARDWARE REV | ～184 |
| GUI INTERFACE | ～186 |
| DEVICE TYPE | ～188 |
| POLARITY | ～189 |
| PRIMARY/SECONDARY | ～190 |
| PARTNER | ～191 |
| OPERATING MODE | ～192 |
| GAGE | ～194 |
| NUMBER OF CONTACTS | ～196 |
| ACTIVE CONTACT LENGTH | ～198 |
| CONTACT SEPARATION | ～202 |

FIG. 21A

| | |
|---|---|
| DISPLAY LENGTH | 204 |
| PHYS CHARACTERISTICS | 208 |
| FDBK LP CNSTNTS | 210 |
| CROSSOVER TEMP | 212 |
| ODOMETER SET POINT | 214 |
| MATCH PART NO. | 218 |
| MATCH CHARACTERISTICS | 220 |
| MATCH ACCEPTABLE TABLE | 222 |
| MATCH LOCKOUT TABLE | 224 |
| PID MULTIPLIER VALUES | 216 |
| ODOMETER | 228 |

FIG. 21B

ELECTRODE ASSEMBLY WITH SEPARATE BIPOLAR CANNULA AND SUPPLY ELECTRODE

CROSS-REFERENCE TO RELATED APPLICATIONS

This application is a divisional of U.S. patent application Ser. No. 11/381,064, filed May 1, 2006, which claims priority to U.S. Provisional Patent Application No. 60/676,092, filed Apr. 29, 2005, the advantages and disclosure of both of which are hereby incorporated by reference.

FIELD OF THE INVENTION

This invention is related generally to an electrode assembly such as an electrode assembly that can be used to perform a denervation procedure. One version of this invention is related to a bipolar electrode assembly that can further be employed to introduce therapeutic agents at the site to which the electrode is applied.

BACKGROUND OF THE INVENTION

Electrosurgical tool systems are used to cut tissue, shape tissue, coagulate tissue and ablate tissue at surgical sites to which the tools are applied. Generally, an electrosurgical tool system includes an electrode with at least one electrically active tip. An electrode that has a single active tip is referred to as monopolar. An electrode with at least two active tips is typically referred to as bipolar. A control console, also part of the system, supplies an RF signal to the electrode. Often this signal is between 50 KHz and 10 MHz. The RF signal is applied to the active tip(s). If the system includes the monopolar electrode, a second dispersive electrode, is placed in contact with the patient to serve as a return path for the RF signal. If the system includes a bipolar electrode, the active tips alternate as active and return poles during the RF cycle.

One medical specialty in which electrosurgical tools are used with increasing frequency is pain management. Pain is felt as a consequence of first, a stimulus being applied to a first nerve. Then, a signal representative of the pain is transmitted from the first nerve through the other nerves in the neural network to the brain. An individual can suffer chronic pain if the biological conditions are such that the first nerve latches into a condition in which it continually transmits the pain signal through the neural network to the brain.

In a pain management process, an electrosurgical tool is used to remove either the initial pain transmitting nerve or one of the associated downstream nerves from the neural network. This disconnection stops the flow of pain messages to the brain. Medically, the process of removing the nerve from the nerve network is called denervation.

In a denervation process, the RF energy emitted by the electrode is applied to the nerve. The nerve absorbs this energy and, as a consequence, is heated to the level at which it ablates.

Presently, the common practice is to use a monopolar electrode assembly to apply the RF energy to the nerve that is to be subjected to ablation. The electrode assembly has two separate components, a cannula and a supply electrode. The cannula is a tube like structure. At the distal end tip, the end positioned at the surgical site, there is an active electrode tip. The supply electrode is inserted in the bore that extends through the cannula. Fitted to the supply electrode is a temperature sensitive transducer.

In the denervation procedure, the surface location above the nerve to be ablated is first anesthesized. The cannula is then inserted through the skin and directed toward the nerve. The supply electrode is fitted to the cannula. A low powered signal is then applied to the supply electrode. This electrode assembly is thus used as a supply electrode to precisely identify the position of the nerve. Once the position of the nerve is determined, the supply electrode is withdrawn from the cannula. An anesthesia is introduced through the cannula to the procedure site in order to numb the tissue at the site. The supply electrode is then reinserted into the cannula. At this time, a higher powered signal is applied through the supply electrode to the active tip integral with the cannula. These high powered RF signals are what are absorbed by and cause the ablation of the nerve.

During the ablation process, the transducer provides an indication of the temperature of the tissue being subjected to ablation. The medical personnel use this information to regulate the application of power to the electrode assembly.

There are many situations however wherein it is desirable to use a bipolar electrode in order to apply RF energy in order to perform the denervation procedure. This is because, the energy flow when using this type of electrode is essentially between the two active tips. Thus the energy flow at the surgical site is more directed than when a monopolar electrode with a large area external ground pad is employed. As a consequence of this more directed energy flow, more energy is applied in a shorter amount of time to the tissue, the nerve, to be ablated. Inversely, less energy is absorbed by nearby tissue that should be subjected to ablation. Thus, using a bipolar electrode to perform the ablation process would further result in a denervation process that is less likely to harm surrounding tissue.

However, to date, there have been obstacles to using bipolar electrodes for denervation procedures. This is because it has proven difficult to provide bipolar electrode assemblies that are relatively small in size. Small diameter electrodes are needed in order to ensure the precision application of the RF energy to the nerve to be ablated. Also, it is desirable to design the electrode so that when inserted into the patient, the skin is exposed to minimal trauma. Large diameter electrodes, with sections having different stepped outer diameters, could potentially cause aggravated trauma to the skin and underlying tissue during the insertion process.

One could provide a bipolar electrode assembly that is solid. Such an assembly would be small in diameter. However, such an assembly would not provide the through bore desirable for introducing anesthesia or agents to the surgical site.

Further different sized and shaped electrode assemblies are available to surgeons. These different sizes and shapes facilitate the position of their distal end tips at the locations where they are to be used to perform treatment. Sometimes the cannulae and supply electrodes appear to match when, in fact, they do not. This requires the medical personnel to take additional time to ensure that the proper cannula and supply electrode pair are assembled together to form the electrode assembly.

SUMMARY OF THE INVENTION

This invention is directed to a new and useful electrode assembly. Many preferred versions of this invention are constructed as bipolar electrodes. The electrode assembly of this invention is further designed to function as conduit through which anesthesia or other agents can be introduced to the surgical site.

In some versions of this invention, the electrode assembly includes a cannula and a supply electrode. In many versions of this invention, the cannula has two electrically spaced active contacts. The supply electrode is dimensioned for insertion in the cannula.

In versions of this invention wherein the cannula has the two tips, the cannula and supply electrode are further constructed, so that as result of the insertion of the supply electrode into the cannula, two conductive paths between the cannula and the control console are established. The first path is through the supply electrode to a first one of the active contacts. The second path is established across complimentary conductors on the cannula and the supply electrode to the second active contact of the cannula.

In alternative versions of the invention, the electrode assembly consists of a cannula and a complementary post. A temperature sensitive transducer is disposed at the distal end of the post. In these electrode assemblies of the invention, the complementary contacts at the proximal end of the cannula and the post establish the electrical path to the active contact.

A memory device, such as a NVRAM or RFID, is integrally attached to each cannula and supply electrode or post. Each memory device contains data identifying the type of cannula, supply electrode or post and its characteristics. Data regarding the operation of the cannula or supply electrode are also stored in the memory. Each memory device integral with a cannula contains data identifying the supply electrodes or supply electrode characteristics with which the cannula can be used. Each memory device integral with a supply electrode contains data identifying the cannulae or cannulae characteristics with which the supply electrode can be used.

A cannula and supply electrode subassembly is connected to the control console. Internal to the control console is a controller. The controller reads the data in the memories of the attached cannula and supply electrode/post. Based on these data, the controller determines if the cannula-supply electrode or cannula-post assembly will function properly. Based on this determination, the control console selectively directs the control console to output to the supply electrode the RF signal needed to perform the intended surgical procedure.

If the cannula and supply electrode (post) are improperly matched, the control console generates a warning message and/or inhibits the outputting of the RF signal.

Based on the data read from the cannula supply electrode memories, the control console also regulates the RF signal that is applied to the supply electrode in order to energize the cannulae active tip(s).

In some versions of the invention, when a supply electrode or post is first selected for use, the control console generates information indicating which complementary cannulae can be used with the selected supply electrode or post. This makes it easier for surgical personnel to quickly determine which complementary component should be selected for use with the selected component.

BRIEF DESCRIPTION OF THE DRAWINGS

These and other objects, features and advantages of this invention will be apparent from the following detailed description of the preferred embodiment and best mode, appended claims, and accompanying drawings in which:

FIG. 10 is an exploded perspective view of the supply electrode assembly;

FIG. 11 is a partial top view of the electrode assembly in the operational state;

FIG. 12 is a partial cross section of the electrode assembly taken along line 12-12 of FIG. 11;

FIGS. 21A and 21B depict the data fields within the memory of a removable component, a cannula or a supply electrode, of the system of this invention;

DETAILED DESCRIPTION

I. Overview

Figure 1:
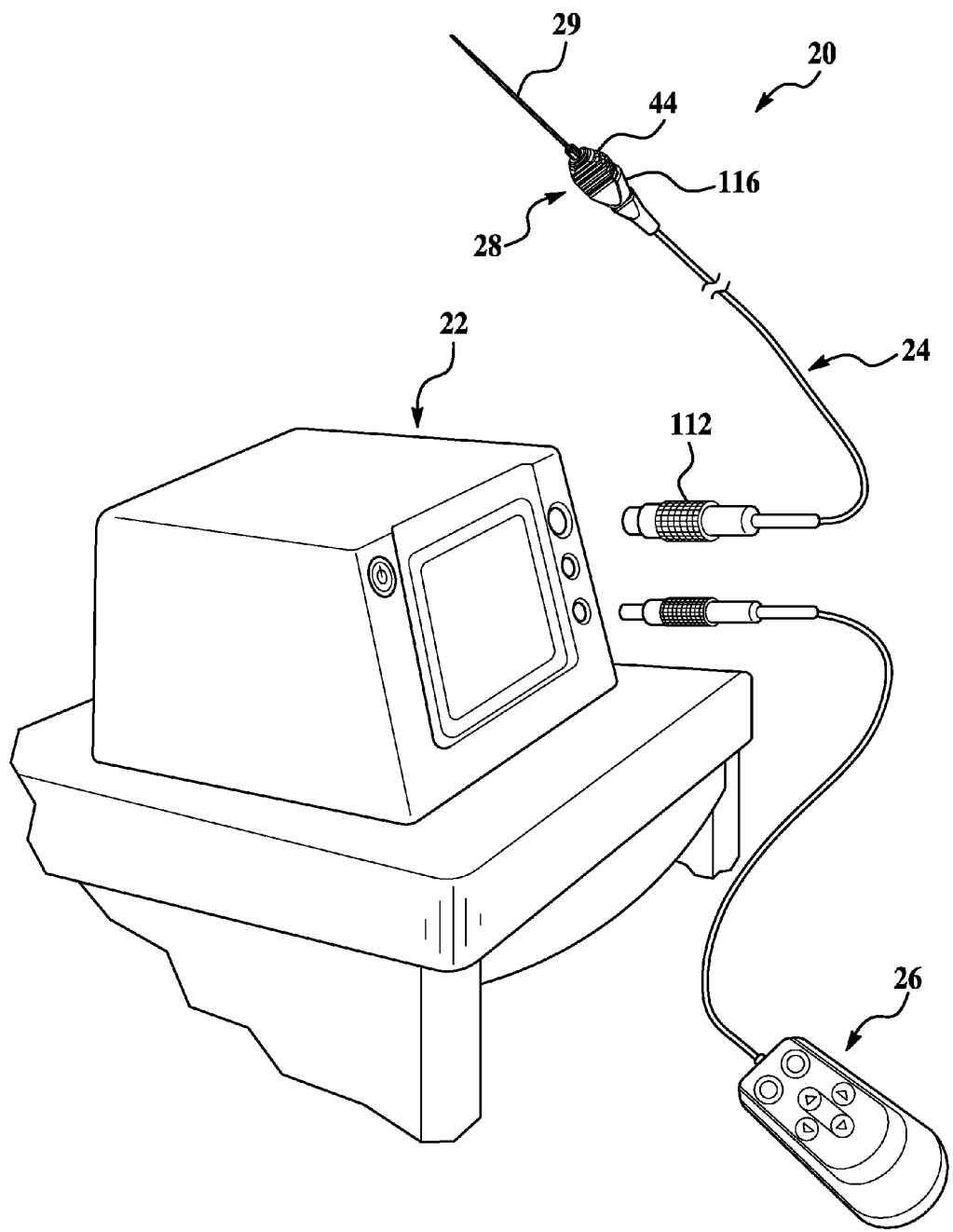
FIG. 1 is a perspective view of a bipolar electro surgical system embodying the present invention.

Referring in more detail to the drawings, FIG. 1 illustrates a bipolar electrosurgical system 20 of the present invention having a control console 22 for generating electrical energy of a controlled radiofrequency. An electrode assembly 24 (also referred to as an electrosurgical tool or electrode tool) of the system 20 plugs into the control console 22 at one end and delivers the radio frequency (RF) energy to a targeted nerve tissue area of a patient at an opposite end. Preferably, the system 20 has a remotely located controller 26 that communicates with and preferably plugs into the control console 22 enabling an operating physician to control multiple functions. Further aspects of the control console 22 are disclosed in U.S. patent application Ser. No. 11/112,702, having the same assignee as the present invention and incorporated herein by reference in its entirety.

In a pain management procedure, system 20 is used to modify nerve cells to the point at which they no longer function. This procedure is called a denervation procedure. In a denervation procedure, the modification of nerve cells is considered to result in the formation of a lesion. In other procedures wherein the system of this invention is used to modify or remove cells, the process is called ablating the tissue. The control console 22 applies preferably temperature-controlled, RF energy into targeted nerve tissue to the electrode assembly 24. The system may also be used in "pulsed mode." Instead of creating heat lesions, RF energy is pulsed with a duty cycle low enough that tissue temperature rise is kept below a level which can kill cells. Pain relief is achieved by influencing the nerve tissue through the pulsed E field. It is theorized that the intense E field created by the pulsed RF influences gene expression in the nerves. This changed gene expression provides a pain reduction. More specifically, the system 20 may be used for selective denervation and tissue destruction procedures that may be performed on the lumbar, thoracic, and cervical regions of the spinal cord, peripheral nerves, and nerve roots for the relief of pain. Examples include, but are not limited to, Facette Denervation, Percutaneous Chordotomy/Dorsal Root Entry Zone (DREZ) Lesion, Trigeminus Neuralgia, and Rhizotomy.

Figure 2:
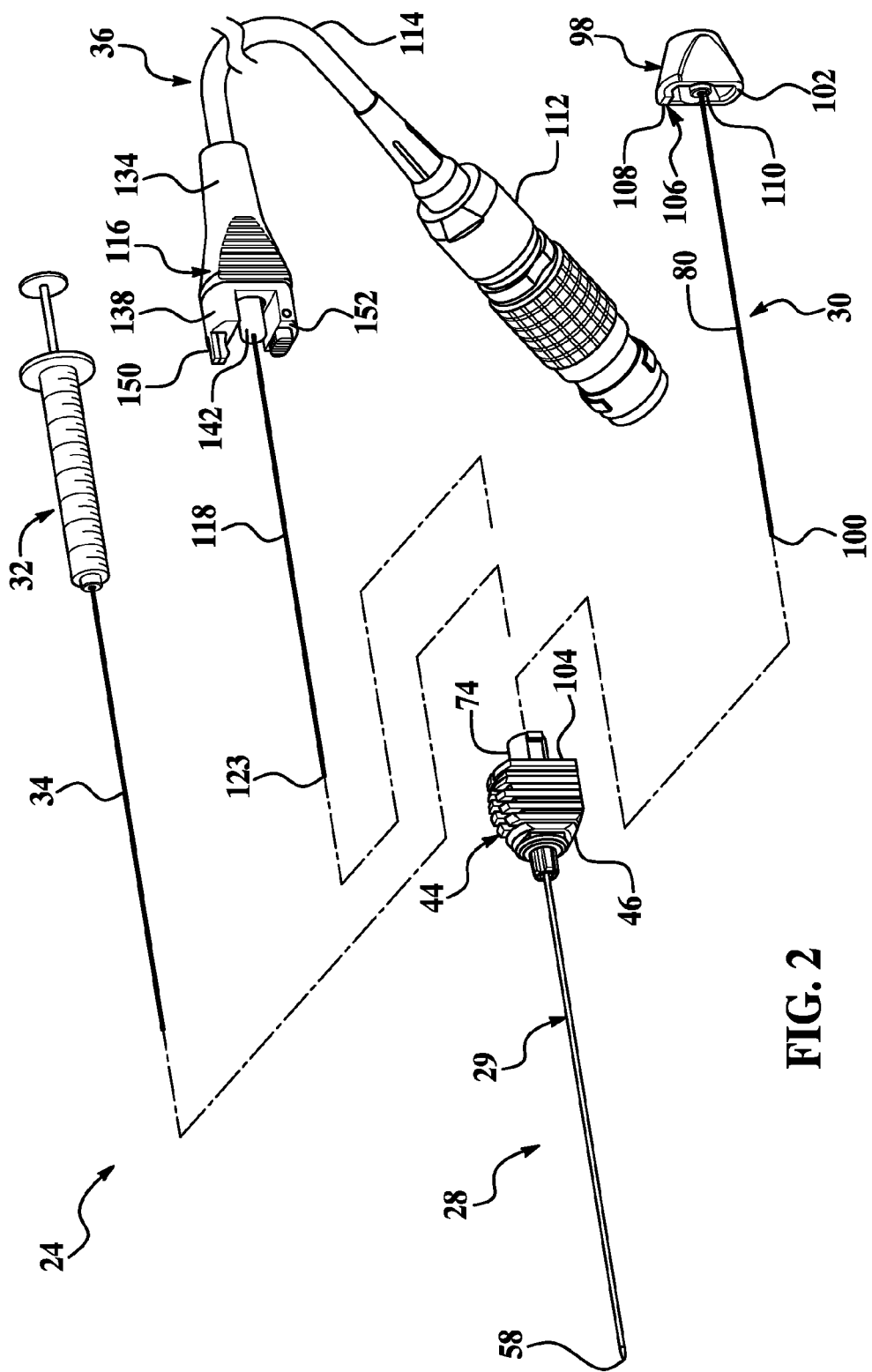
FIG. 2 is an exploded perspective view of an electrode assembly of the system having a cannula, a stylet, a syringe and a supply electrode.

Referring to FIG. 2, the electrode assembly 24 has a cannula 28 and a supply electrode assembly 36. The cannula 28 and the supply electrode assembly 36 are preferably separate components that releasably mate to one another during the denervation procedure, and the cannula 28 is preferably bipolar when electrically active, however, a modification of the present invention may also utilize monopolar cannula when electrically active. A stylet 30 also seen in FIG. 2 is used to fit the cannula to the surgical site at which the procedure is to be performed. Also shown in FIG. 2 is a syringe 32 and a complementary hypodermic needle 34. Once the cannula 28 is properly placed, the syringe may be used to introduce anesthesia or another drug at the site at which the procedure is performed. Needle 34 is sometimes inserted in the cannula 28 to function as the conduit for introducing the drug. Thus, while stylet 30, syringe 32 and needle 34 may be used with cannula 28 of this invention, it is understood they are not part of the invention.

Figure 3:
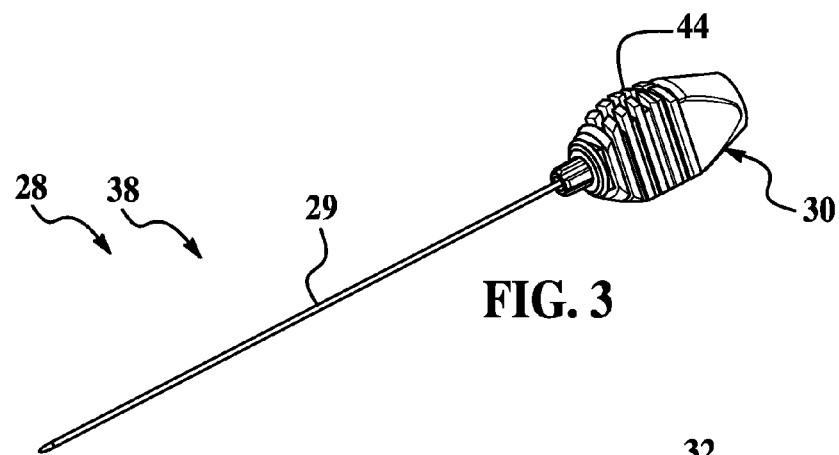
FIG. 3 is a perspective view of the stylet inserted in the cannula designating the tool in a tissue penetrating state of the system.
Figure 4:
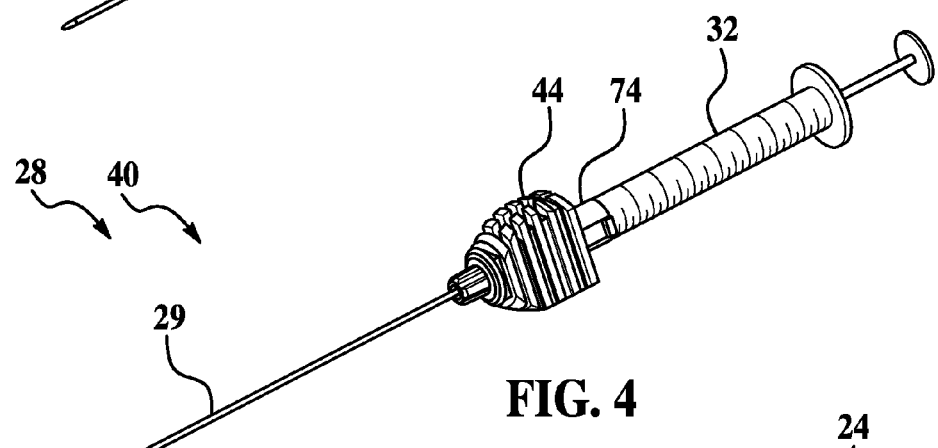
FIG. 4 is a perspective view of the syringe mounted to the cannula designating the tool in an anesthetic state.
Figure 5:
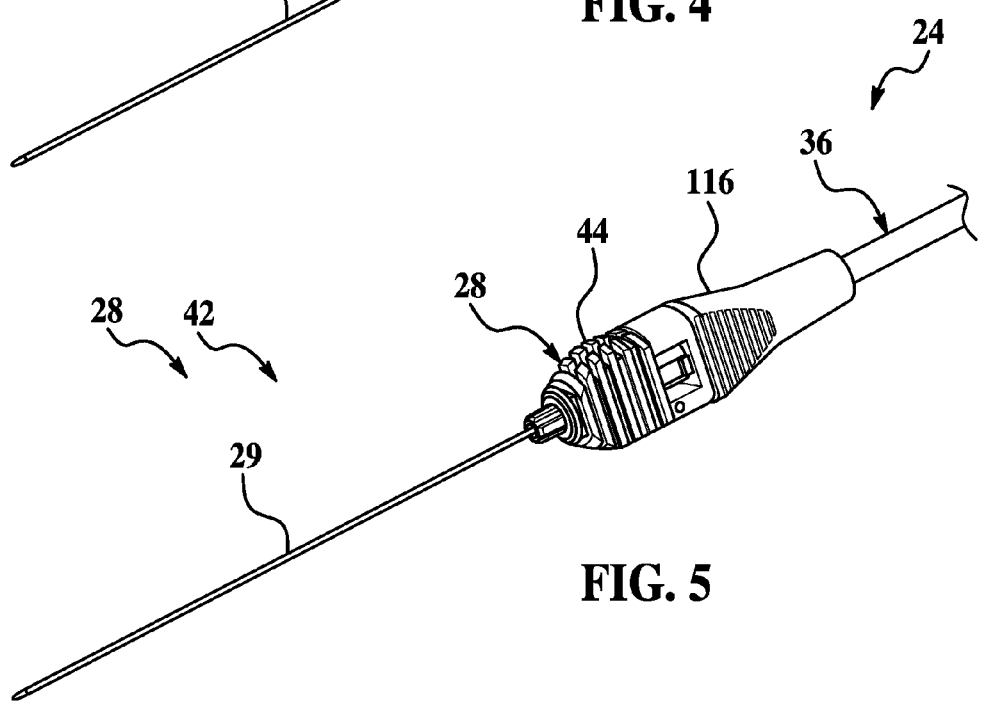
FIG. 5 is a perspective view of the supply electrode inserted in the cannula designating the tool in an operational state.

As best shown in FIG. 3, the cannula 28 is preferably pre-packaged with the stylet 30 inserted in the cannula 28. This orientation of the tool 24 is referred to as a staging or insertion state 38. Generally, when in the insertion state 38, the cannula 28 is best suited to pierce and penetrate skin and tissue to appropriately position the cannula 28 with respect to a nerve targeted for denervation. Upon completion of the denervation procedure, the cannula 28 and the stylet 30 are preferably discarded. As best shown in FIG. 4, after insertion of the cannula 28 into the tissue, the stylet 30 is removed and the syringe 32 is inserted or press fitted to the cannula 28 for localized injection of an anesthetic. This is generally referred to as the medication state 40. Once the nerve tissue targeted for denervation and the surrounding area is properly medicated, the syringe 32 is removed from the cannula 28 and the cannula 28 remains in the tissue. As best shown in FIG. 5, after medication the supply electrode assembly 36 is attached to the cannula 28 for the conduction of energy to the nerve tissue targeted for denervation. This orientation of the tool 24 is referred to as an operational state 42. When the denervation procedure is completed, the supply electrode assembly 36, unlike the disposable cannula 28, is withdrawn from the cannula 28 for sterilization and reuse. Thus, it should be understood that the supply electrode assembly 36 of this invention is able to be subjected to a sterilization process so that post sterilization has a sterilization assurance level (SAL) of at least $10^{-6}$. This means that there is equal to or less than one chance in a million that a single viable microorganism is present on the sterilized item. This definition of sterile is the definition set forth in the ANSI/AAMI ST35-1966, *Safe handling and biological decontamination of medical devices in health care facilities and nonclinical settings*.

During the medication state 40, fluids that may be injected into the tissue via the cannula 28 include fluoroscopic contrast fluids, local anesthetics and steroids. Preferably, the signal emitted by the cannula 28 and generated by the control console 22 is a high powered radio signal having a frequency between 100 kHz and 10 MHz and at power range of between 2 to 200 Watts. In a denervation procedure the RF signal emitted by the cannula is typically at a power level of less than 50 Watts and more often less 20 Watts.

II. Bipolar Cannula

Referring to FIGS. 6-9 and 15-16, the bipolar cannula 28 has a generally tubular body 29, which is generally a multi-layered needle, projecting axially forward along an axis 50 from a coupling assembly 44 of the cannula 28. The coupling assembly 44 has an electrically insulated hub 46 that is generally ribbed for gripping by the user or physician. Body 29 is mounted to the hub 46 and has a conductive inner tube 48, an inner electrical insulating sleeve 52, an electrically conductive outer tube 54 and preferably an electrical insulating outer sleeve 56. The inner tube 48 preferably defines a substantially straight and axial extending through-bore 57 (see FIG. 9), and projects axially forward to a distal end 58. The inner tube 48 is electrically insulated from the outer tube 54 by the inner sleeve 52 that is tube shaped. Insulating inner sleeve 52 is oriented concentrically to and radially outward from the inner tube 48 and projects axially from the hub 46 to a generally annular distal end 60 located adjacent to and trailing the distal end 58. Because inner insulating sleeve 52 does not extend axially forward as much as the inner tube 48, a ring shaped portion of the inner tube 48 at the most distal end of the tube is exposed to the environment. This section of inner tube 48 is the first active contact or electrode terminal 62 of cannula 28.

Outer tube 54 of the body 29 is spaced radially outward from the inner tube 48 by the inner insulating sleeve 52 and preferably projects axially forward to a distal end 64. Outer tube distal end 64 is spaced proximally rearward from the inner tube active contact 62. Insulating outer sleeve 56 is preferably a tubular jacket orientated concentrically to and radially outward from the outer tube 54 and projecting axially from the hub 46 to a generally annular distal end 66 located adjacent to and trailing the distal end 64. Because the outer sleeve 56 does not extend axially forward as much as outer tube 54, there is ring shaped exposed section of the sleeve 56 at its distal end 64. This section of outer tube 54 is the second active contact or electrode terminal 68. When a potential is applied across contacts 62 and 68, a RF energy field develops between the contacts 62, 68 thereby sending a current through the tissue and completing the circuit.

The insulating inner and outer sleeves 52, 56 are preferably heat shrinkable tubing made of a polyester or Teflon material having a wall thickness of about 0.0008 inches to 0.0012 inches. With regard to the inner and outer tubes 48, 54, the first active contact 62 of the inner tube 48 is preferably the supply or power electrode terminal and the second active contact 68 is preferably the return or ground electrode terminal. However, one skilled in the art would now know that the electrical charge of the contacts 62, 68 can be reversed. Moreover, the control unit 22 may function to fluctuate polarities.

Figures 15, 16:
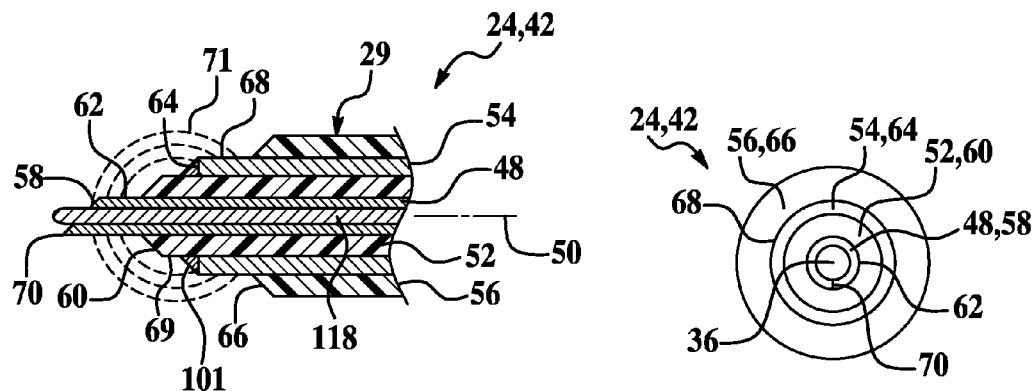
FIG. 15 is an enlarged, partial, cross section of the electrode assembly in the operational state taken from circle 15 of FIG. 12.
FIG. 16 is an end view of the electrode assembly in the operational state.

Referring to FIG. 15, because first active contact 62 and the second active contact 68 are separated axially by an insulating ring 69 of the insulating inner sleeve 52, a current path or energy field 71 is generated between the contacts 62, 68 by the control console 22 when the tool 24 is in the operating state 42 thus creating a lesion in the target tissue. The size of the lesion can be varied by changing or varying an axial length of any one of the exposed contacts 62 and 68 or insulating ring 69 which alters the current path 71. Consequently, a surgeon can select an appropriate cannula 28 that meets his or her particular needs.

Because physicians are typically familiar with the lesion sizes formed by active tips of monopolar systems unlike the present invention, the axial spacing of the exposed bipolar contacts 62 and 68 or insulating ring 69 can be referenced as equivalents to known active tip lengths of monopolar systems, such that physicians can use the bipolar system 20 and get the same results as they may have using a known monopolar device. Testing has been completed for this purpose with the results reproduced as follows:

| Length (mm) of Contact 62, Ins. Ring 69, Contact 68 | Equivalent Active Tip Length (mm) | Bipolar Cannula Diameter |
| --- | --- | --- |
| 2.3, 1.3, 9 | 2.5 | 20 G |
| 3.5, 15, 10 | 2.5 | 20 G |
| 2, 2, 2 | 5.0 | 20 G |
| 3.5, 2.5, 6 | 5.0 | 20 G |
| 2.8, 2.8, 2.8 | 7.5 | 20 G |
| 5, 4, 5 | 10 | 20 G |
| 6, 5, 6 | 15 | 20 G |

It should be appreciated that the above 20 G (20 Gauge) diameter is the outer diameter of the insulating outer sleeve 56. This diameter is exemplary, not limiting. Other cannulae of this invention, both monopolar and bipolar, may have outer diameters ranging from 12 G to a smaller diameter 26 G. For electrode assemblies 24 used for denervation procedures, the diameter of the cannula 28, which is the diameter of the supply electrode assembly 36, is preferably 16 G or more and more preferably 18 G or more.

Notably, multiple variations of the axial lengths of exposed contacts 62 and 68 and ring 69 results in generating similarly sized lesions. Testing shows that having a much longer outer tube exposed contact 68 relative to the inner tube contact 62 results in the lesion being concentrated about contact 62. "Longer" it is understood here means that contact 68 has a length two (2) times or more and often three (3) times or more than the length of contact 62. If active contacts 62 and 68 are equal in size and insulating ring 69 is of equal length or smaller in length than a single one of the contacts, during a denervation procedure, the lesion forms around both contacts and the insulating ring.

To facilitate smooth skin piercing, the inner tube distal end 58 is beveled or chamfered to a point 70 similar to that of a hypodermic needle. Furthermore, the distal ends 60 and 66 of the insulating inner and outer sleeves 52, 56 are tapered, (tapers not identified). Moreover, distal end 64 of the conductive outer tube 54 that forms second active tip 68 preferably has an annular taper 101 around its outer distal face. This tapering substantially reduces or prevents snagging of tissue upon the cannula when the cannula is being inserted thus reducing tissue trauma.

It should be recognized alternative means may be employed to minimize the trauma associated with the insertion of the distal face of outer tube 54. Instead of a complete taper, outer tube 54 may be formed with a bevel around its outer perimeter. Alternatively, an adhesive, a plastic or a heat shrink wrapper may be positioned immediately forward of the distal end face of outer tube 54 to form an angled surface that minimizes the trauma associated with the insertion of the outer tube.

Referring to FIGS. 2 and 6-9, the hub 46 of the coupling assembly 44 of the cannula 28 is preferably made of injection molded plastic that may be molded directly to at least one of the proximal ends of the sleeves 52, 56 and tubes 48, 54 or is attached by adhesive. Preferably, the hub 46 has a counter-bore 72 located rearward of and concentrically to the through-bore 57 and defined by a rearward projecting collar 74 of the hub 46. The counter-bore 72 has a funnel portion 76 that tapers radially inward and forward toward a trailing opening 78 of the through-bore 57. The counter-bore 72 with the funnel portion 76 assist in guiding a solid rod 80 of the stylet 30, the hypodermic needle 34 of the syringe 32, and the leading portion of the supply electrode assembly 36 into the small through-bore 57 for the various states 38, 40, 42 of the denervation procedure.

Figure 6:
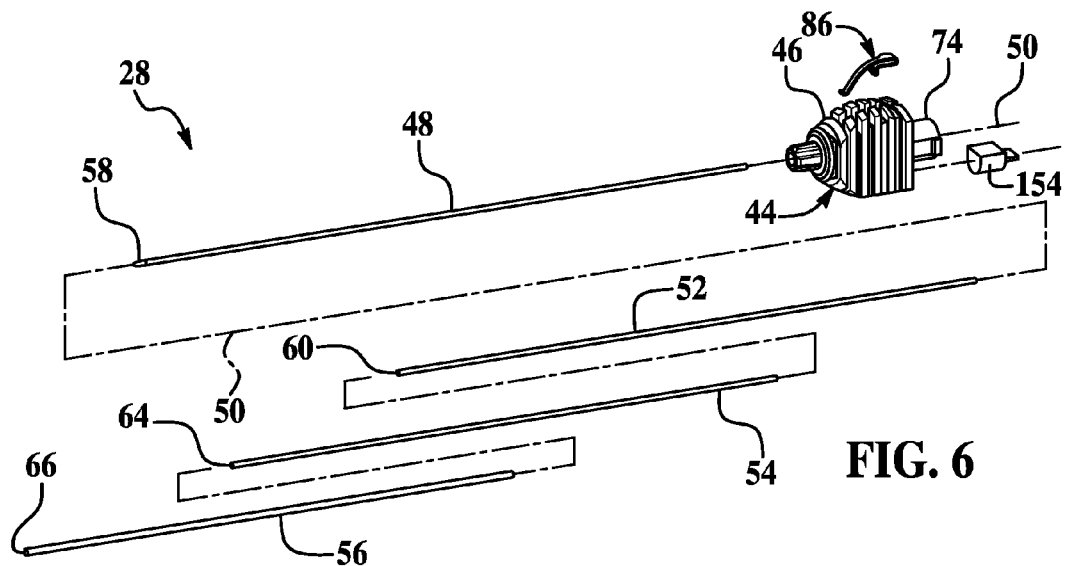
FIG. 6 is an exploded perspective view of the cannula.
Figure 7:
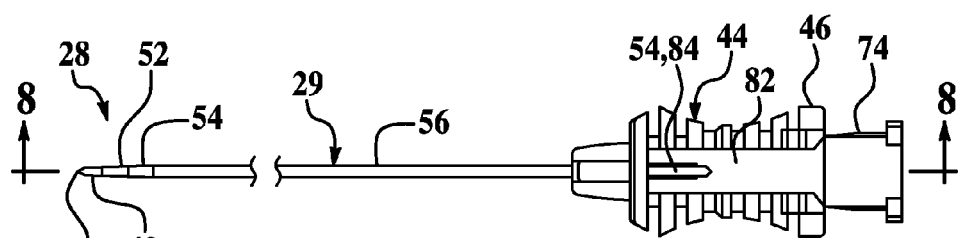
FIG. 7 is a top view of the cannula with a terminal removed to show internal detail.
Figure 8:
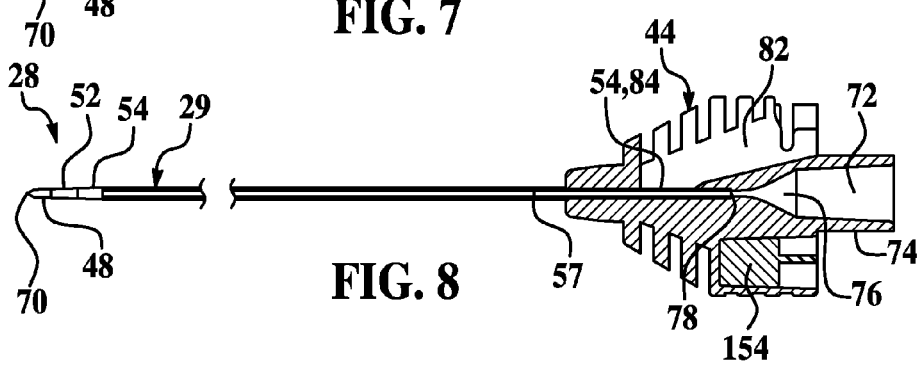
FIG. 8 is a cross section of the cannula taken along line 8-8 of FIG. 7.
Figure 9:
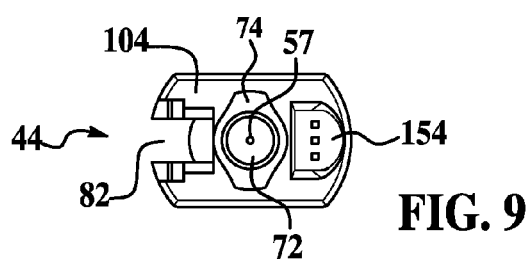
FIG. 9 is a trailing end view of the cannula.
Figure 18:
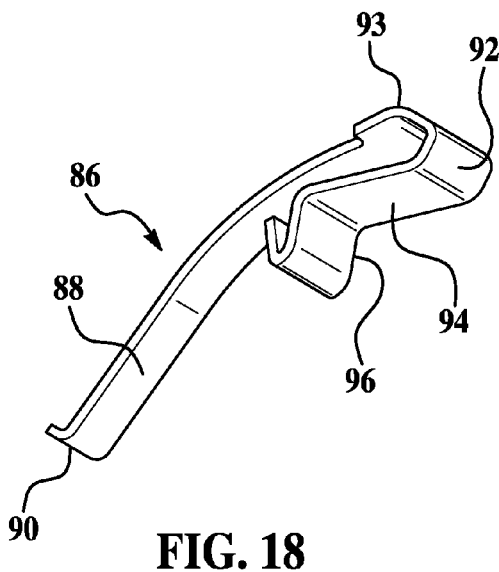
FIG. 18 is a perspective view of the terminal of the cannula.

An alcove 82 in the hub 46 of the cannula coupling assembly 44 opens radially outward and axially rearward. The alcove 82 is separated from the counter-bore 72 in the hub 46, as shown in FIG. 8. Exposed generally through a bottom or window 84 of the alcove 82 defined by the hub 46 is outer tube 54. As best shown in FIGS. 6 and 18, a resiliently flexible terminal 86 of the coupling assembly 44 seats to the hub 46 and is generally biased against the tube 54 forming an electrical connection. Referring to FIG. 18, the terminal 86 has an elongated bowed arm 88 that extends axially between a leading cupped end 90 having a convex surface that is in sliding contact with the ground tube 54. A contact pad 93 extends forward and downwardly from bowed arm 88. Contact pad 93 leads to a curved elbow or resilient pivoting joint 92. Extending axially forward from the elbow 92 and radially inward from the arm 88 is a leg 94 that rests upon the hub 46 to radially aligning the contact pad 93. An opposite trailing end or tab 96 projects radially inward from a forward end of the leg 94 for axial alignment of the terminal 86 with respect to the axis 50.

During manufacturing of the body 29 of the cannula 28, the inner tube 48 is cut to length and the bevel at end 58 is cut to form point 70 then the outer tube 54 is cut to length. The inner and outer insulating sleeves 52, 56 are then preferably cut to an approximate length and slide over the respective inner and outer tubes 48, 54 and preferably adhered with glue. Since the sleeves 52, 56 are preferably of a heat shrink type, the tubes 48, 54 with glued sleeves 52, 56 are individually sent through a heating coil to shrink and thus seat the sleeves 52, 56 to the respective tubes 48, 54. The tubes 48, 54 are then individually placed into a fixture and the appropriate amounts of insulation from the sleeves 52, 56 are stripped off the tubes 48, 54 to expose the required axial lengths of ring-shaped contacts 62, 68.

The leading taper of the heat shrunk sleeves 52, 56 is then preferably formed by applying a mild abrasive material such as light sandpaper to the sleeves already seated on the tubes. The abrasive may be a paper-backed sand paper that after applied, results in a smooth radial transition between the sleeves and tubes. The outer tube 54 is then slid axially over the inner sleeve 52 and the ramped annular bead or taper 101 preferably of UV cured adhesive is added between the inner sleeve 52 and the outer tube 54 to further smooth-out the leading radial transition of the body 29.

In some versions of the invention, the outer tube 54 has a thinner wall than that of the inner tube 48. This allows the use of a larger sized inner tube 48, while maintaining a slim overall dimension of the body 29. Preferably, the inner sleeve 52 after heat shrinking is about 22 gauge and the outer sleeve 56 after heat shrinking is about 20 gauge. The proximal end of the body 29 is then inserted into an axially extending hole in the hub 46 of the cannula 28 and is connected to the hub preferably by an adhesive. The distal ends of the insulating sleeves 52, 56 are then sanded to achieve a taper, thus reducing tissue trauma during insertion of the body 29 when in use.

Finally, the bowed terminal 86 is inserted into the alcove 82 defined through a side of the hub 46. The terminal 86 is positioned such that its forward distal end 90 is electrically contacting the outer tube 54 (the outer tube 54 is exposed in the window 84 to make this contact). Terminal 86 is secured in the window 84 by a dimple and/or adhesive added between the leg 96 of the terminal and the hub 46.

Inner and outer tubes 48 and 54, respectively, are preferably formed of a conductive material, more preferably 304 stainless steel. Insulating sleeves 52 and 56 are preferably formed of polyester heat shrink (PET). The adhesive used to bond the cannula hub 46 to the body 29 is an UV adhesive, more preferably from the urethane (meth)acrylate class. The hub 46 may also be bonded using an instant adhesive such as ethyl cyanoacrylac.

III. Stylet

Figure 13:
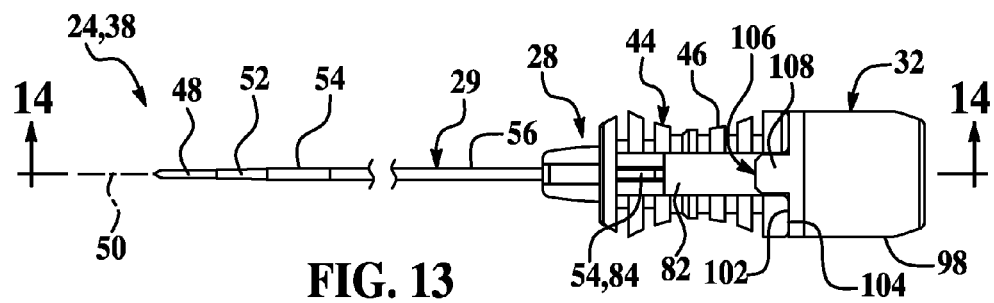
FIG. 13 is a top view of the tool in the tissue penetrating state with the terminal of the cannula removed to show internal detail.
Figure 14:
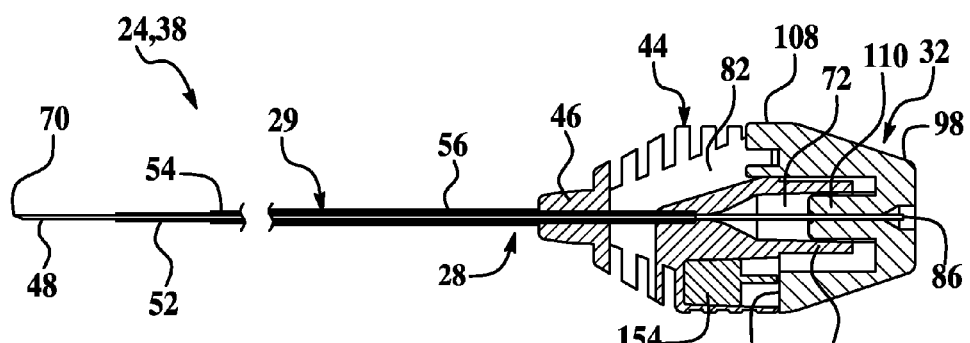
FIG. 14 is a cross section of the tool in the tissue penetrating state taken alone line 14-14 of FIG. 13.

As best illustrated in FIG. 2, the rod 80 of the stylet 30 projects forward from an enlarged head or cap 98 of the stylet 30 and to a leading distal end 100 of the rod 80. Preferably, the rod 80 is made of a corrosion resistant and flexible metal that resists plastic deformation such as stainless steel and the cap 98 is made of injection molded plastic. When in the tissue penetrating state 38 (see FIGS. 3, 13 and 14), a forward facing stop 102 carried by the cap 98 is in contact with a rearward facing stop 104 carried by the hub 46 of the cannula 28. This axial alignment of the cannula 28 to the stylet 30 when in the tissue penetrating state 38 axially aligns the distal end 100 of the solid rod 80 to the distal end 58 of the inner tube or tube 48. Preferably, the distal end 100 is chamfered or beveled at an angle substantially the same as the angle of the distal end 58.

To assure the bevels of the ends are properly aligned circumferentially, a circumferential indexing feature 106 is carried between the hub 46 of the cannula 28 and the cap 98 of the stylet 30. Indexing feature 106 preferably has a tab 108 formed unitarily to and projecting forward from the cap 98 and snugly into the alcove 82 of the hub 46 radially outward from the terminal 86. With both ends beveled, the combination forms a leading flush face that enhances the ability of the tool 24 to pierce through tissue when in the tissue penetrating state 38, and without introducing tissue fluids and matter into the through-bore 57 of the body 29 of device 28. Moreover, with the rod 80 of the stylet 30 in the through-bore 57, the rigidity of the body 29 is enhanced for purposes of penetration.

A post 110 of the cap 98 projects axially forward and is disposed substantially concentrically to the axis 50. During manufacturing, a proximal end of the rod 80 is inserted into a concentric hole in the post 110 and is preferably secured therein with an adhesive. Alternatively, the cap 98 may be injection molded directly to the rod 80. When the stylet 30 is mated to the cannula 28, the post 110 snugly fits in the counter-bore 72 of the hub 46. Because the post 110 does not project axially as far as the counter-bore 72, an axial distance or clearance exists between the distal end of the post 110 and the bottom of the counter-bore 72 or hub 46. This clearance reduces the potential for shear forces placed upon the rod 80 if the rod and the through-bore 57 are slightly laterally misaligned. This clearance also assures that the cannula 28 and the stylet 30 do not unintentionally un-mate from the tissue penetrating state 38 as a result of any undue shearing force.

IV. Supply Electrode

As seen in FIG. 10 the supply electrode assembly 36 is connected by a cable 114 and a plug 112 to the control console 22. Internal to cable 114 are a plurality of insulated conductors 115. A supply electrode 118 of the electrode assembly 36 extends from a housing 134 attached to the proximal end of cable 114. Generally, the plug 112 removably connects to the control console 22. The cable 114 extends flexibly between the plug 112 and the coupling assembly 116, and the supply electrode 118 is supported by and projects outward from the coupling assembly 116.

The supply electrode 118 serves as the component that completes the conductive path from control console 22 through plug 112 and cable 114, to the first active contact 62 of the cannula 28. Supply electrode 118 also functions as a housing for a temperature sensitive transducer 120, here, a thermistor (see FIG. 17). Supply electrode 118 includes an elongated hollow body or shell 122 preferably formed of high strength, electrically conductive material such as stainless steel or a memory metal such as a nickel-titanium alloy. One potential nickel-titanium alloy from which shell 122 can be formed is sold under the trademark NITINOL. Shell 122 is preferably cylindrical and shaped such that, when the supply electrode 118 is inserted in the through-bore 57 of the body 29, a substantially cylindrical outer wall 124 of the hollow shell 122 is in physical contact with a substantially cylindrical inner wall of the electrode tube 48. The supply electrode shell 122 is further shaped, so that when the supply electrode 118 is fully inserted in the body 29 (i.e. the operational state 42), a sealed distal end 123 of the shell 122 of the supply electrode 118 is located at the open distal end of the through-bore 57 near point 70 of inner tube 48. One skilled in the art would now know, however, that completion of the electrical circuit between the inner tube 48 of the body 29 and the coupling assembly 116 of the supply electrode assembly 36 could be made with mating terminals supported by respective coupling assemblies 44, 116.

Preferably, the Nitinol shell 122 of the supply electrode 118 is formed from a tube with an interior surface of the tube being scrubbed and smoothed by the flow of a slurry during manufacturing. Polishing of the tube in this way makes it easier to insert the temperature sensor 120 into the shell 122. With the interior surface of the tube polished, the tube is cut to length and the distal end 123 is sealed preferably by plasma welding or other appropriate means.

Temperature transducer 120 is a device such as a thermocouple or a thermistor. The output signal from transducer 120 is output through coupling assembly 116, through cable 114 and into the control console 22. This signal provides a temperature reading for the physician. The temperature signal may be used as input signal for a feedback control loop to regulate the characteristics of the RF signal output by console 22. In some systems, the physician can use the temperature data to manually regulate console operation.

Figure 17:
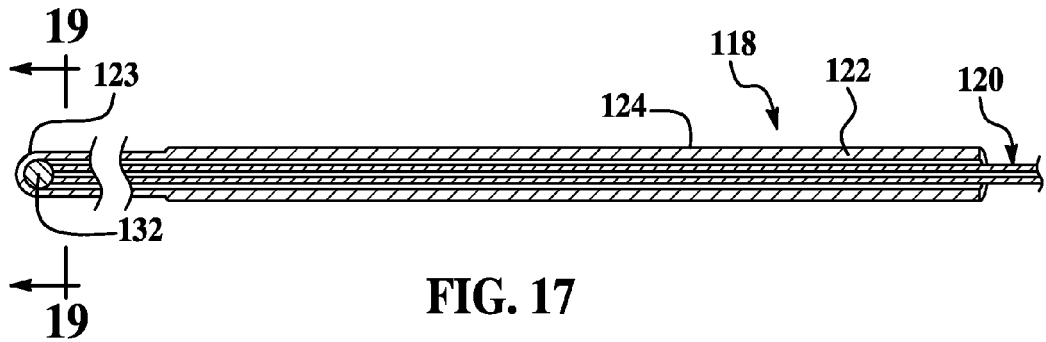
FIG. 17 is an enlarged, partial, cross section of the supply electrode assembly taken from circle 17 of FIG. 10.
Figure 19:
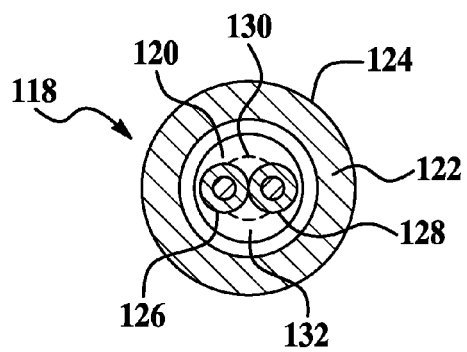
FIG. 19 is a section view through the supply electrode taken along line 19-19 of FIG. 17.

Referring to FIGS. 17 and 19, the temperature sensor 120 comprises two insulated thermocouple wires 126, 128 preferably of a K-type that each have a stripped end leads located at the sealed distal end 123 of the shell 122. Preferably, the wires 126, 128 are coated with Teflon to reduce or prevent any potential for breakage and/or electrical shorts. In one version of the invention K-Type thermocouple wire is employed. The end leads are welded together to form a thermocouple junction 130, shown in phantom in FIG. 19. Thermocouple junction 130 is encased in an electrically insulating bulb 132. In one version of the invention, bulb 132 is formed by coating the thermocouple junction 130 in epoxy. In preferred versions of the invention, bulb 132 is relatively thin. More specifically, the outer diameter of the bulb does not exceed the combined outer diameters of the wire insulated wires 126, 128. During manufacturing, once the temperature sensor 120 is formed, the bulb 132 of the sensor 120 is seated at the sealed distal end 123 of shell 122 with an adhesive, as best shown in FIG. 17. Preferably, bulb 132 seats against the inner surface of the shell 122 at the end 123.

Referring to FIG. 10, the coupling assembly 116 of the supply electrode assembly 36 has an outer housing 134, a carrier 136, a cartridge 138 and an electrical terminal 140. The outer housing 134 is preferably ribbed for improved gripping by a physician during use. The housing 134, carrier 136 and cartridge 138 are preferably formed of an electrically insulating thermoplastic material, more preferably, polyetheretherketone (PEEK). The housing 134 and cartridge 138 are rigidly secured together preferably by an adhesive. The carrier 136 is generally housed by the housing 134 and is located axially rearward of the cartridge 138. The terminal 140 is seated to and supported by the cartridge 138.

Similar to the post 110 of the stylet 30, the carrier 136 has a forward projecting post 142 that projects through the cartridge 138 and is disposed concentric to the axis when in the operation state 42. Shell 122 of the supply electrode 118 is supported by and extends coaxially through the post 110. Preferably, the carrier 136 has a cavity 144 located rearward of the post 142 and opened laterally outward for making and accessing electrical connections during manufacturing. Similar to the cap 98 of the stylet 30, a circumferential indexing feature 146 and axial indexing feature 148 are carried between the coupling assembly 44 of the cannula 28 and the cartridge 138. Indexing feature 146 has a tab 150 projecting forward from the cartridge 138 and snugly into the alcove 82, or indexing feature, of the coupling assembly 44. Indexing feature 148 is the planar forward facing surface of cartridge 138 with which hub stop 104 aligns. Feature 148 thus limits axial movement of cannula 28 relative to supply electrode assembly 36. Tab 150, it should be appreciated also facilitates alignment of the cannula upon its decoupling from the supply electrode. This reduces shear stresses on the supply electrode 118 so as to increase the extent to which the supply electrode 118 can be reused.

It should be understood that the cannula 28 and supply electrode assembly 36 are constructed so that when assembled together to form electrode assembly 24, the actual supply electrode 118 abuts the inner wall of inner tube 48 that defines bore 57. In one version of the invention, inner tube 48 is constructed so that bore 57 has a diameter of 0.018 inches and the complementary supply electrode 118 has a diameter of 0.016 inches. Thus, in this construction of the invention the surface-to-surface clearance between the cannula inner tube 48 and the supply electrode 118 is 0.002 inches. In versions of the invention wherein the supply electrode 118 is made from Nitinol alloy or other flexible material the clearance between these two components may be greater than this amount. Generally, it is believed the maximum clearance should be 0.010 inches or less and preferably 0.005 inches or less. This should insure that, upon insertion of the supply electrode 118 into the inner tube 48, there is sufficient surface contact between the components. Similarly, a minimal surface clearance of 0.0005 inches and more often 0.001 inches between these components is desirable. This minimal clearance facilitates the slidable insertion and removal of the supply electrode 118 into and out of the cannula 28.

V. Memory

Referring to FIGS. 8-10 and 12, preferably adhered in or press fitted into a pocket in the hub 46 of the coupling assembly 44 of the cannula 28 is a non-volatile memory device (NVRAM$_c$) 154. A multi-pin contactor 156 is supported by the cartridge 138 and mates to rearward projecting pins of the NVRAM$_c$ 154 when the coupling assemblies 44, 116 mate. An associated NVRAM$_E$ or RFID chip 155 (see FIG. 10 shown in phantom) is preferably housed in the plug 112 and communicates with the NVRAM$_c$ 154 and control console 22. The NVRAM$_E$ 155 stores data used to regulate the operation of the supply electrode assembly 36. Generally, the NVRAM$_c$ 154 contains data used to match the cannula 28 to the supply electrode assembly 36 and to generally regulate the operation of the system 20. The NVRAMs 154, 155 can also be utilized to store data required to establish integration and derivative constants for an algorithm of the control console 22 that processes temperature sensed by the temperature sensor 120.

Figure 20:
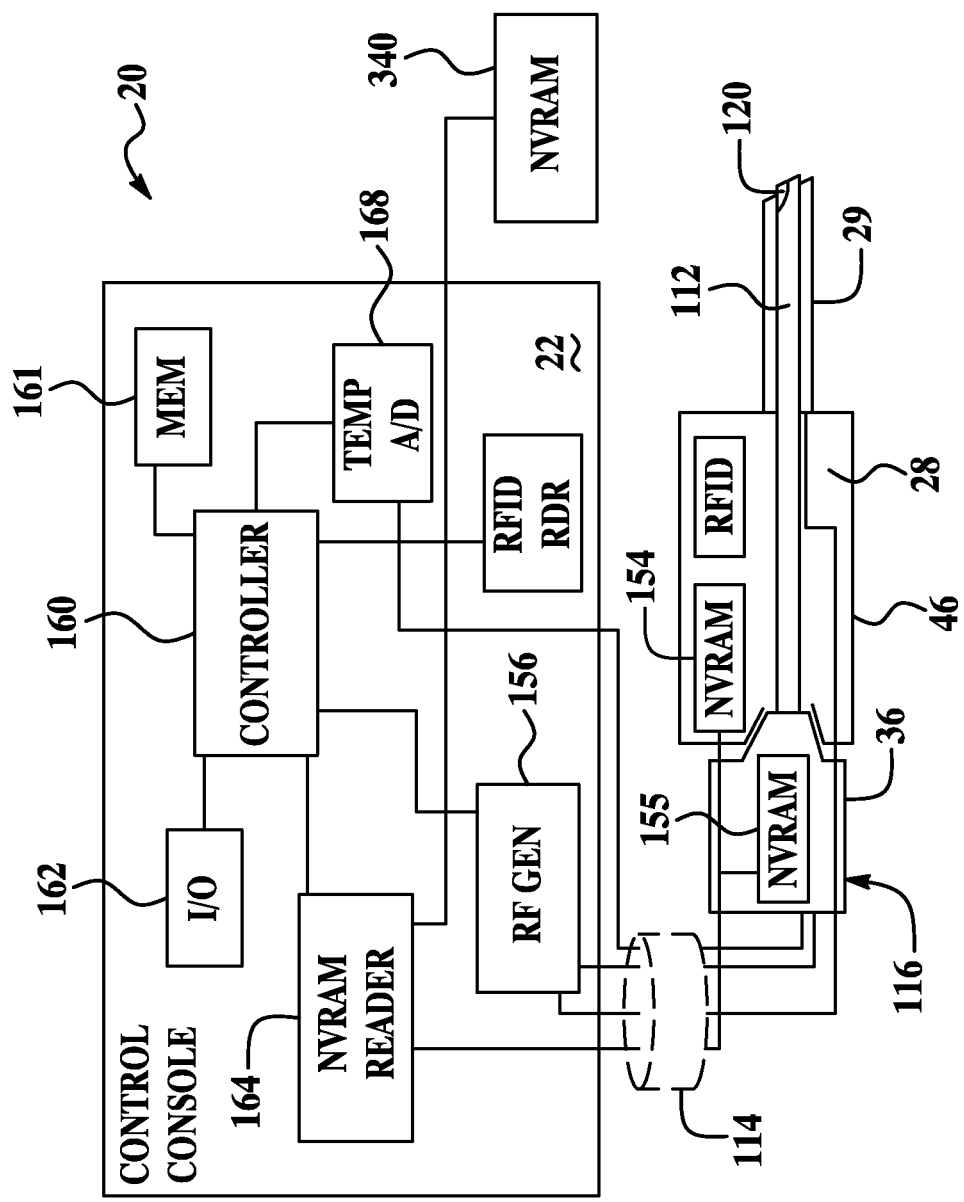
FIG. 20 is block diagram of the electrically active components of the electrosurgical tool system of this invention.

FIG. 20 illustrates the components internal to control console 22 and their relationship to NVRMS 154 and 155. The actual energization signal applied to the electrode 22 is supplied by an RF signal generator 156 internal to the control console 22. The operation of the RF signal generator 156 is regulated by a microcontroller or a system of microcontrollers, µ controller 160 in Figures. One suitable control processor that can be employed as microcontroller 160 is the PIC18F6720 available from Microchip Technology Inc. The microcontroller 160 or system of microcontrollers 60 regulates the actuation of the system 20 based on surgeon-entered command signals. A generic command input/output (I/O) module 162 receives the surgeon-entered commands from either remote controller 26, the screen if the screen is touch screen or any control knobs. The signals generated by I/O module 162 are forwarded to the microcontroller 160. Microcontroller 160 further regulates the operation of the system 20 based on the data read from the cannula NVRAM$_c$ 154 and the supply electrode NVRAM$_E$ 155.

Also internal to control console 22 is a memory 161. Memory 161 stores the operating instructions executed by the microcontroller 160. The memory 161 also stores the data read from the NVRAMs 154 and 155 as well as certain lookup data, discussed below, referenced by the microcontroller 160. Memory 161 is shown as a generic memory unit. It is understood that memory 161 may contain both memory units in which data are permanently stored and units in which data are temporarily stored.

Cable 114 also contains the conductors that connect NVRAMs 154 and 155 to control console 22.

Cable 114 extends from the control console 22 to the coupling assembly 116 of the supply electrode assembly 36. Internal to cable 114 is a conductor of the plurality of conductors 115 that carries the power signal generated by RF generator. Cable 114 also contains a conductor of the plurality of conductors 115 that functions as a RF return path from the coupling assembly 44 of the bipolar cannula 28. Two conductors of the plurality of conductors 115 are part of a one wire bus over which data are read from and written to the NVRAMs 154, 155. Another two data conductors of the plurality of conductors 115 are used to transmit analog signals from the temperature sensor or thermocouple 120 to the control console 22. For simplicity, all of the plurality of conductors 115 are not illustrated in FIG. 12. Additional conductors could be provided to facilitate switching, control, or navigation functions located on the supply electrode assembly 36 and/or cannula 28.

The cannula coupling assembly 44 also has a similar terminal or conductor that extends from NVRAM$_c$ 154 that terminates at a separate contact pad. The coupling assembly 116 of the supply electrode assembly 36 has contact pads that are complementary to the above two contact pads. The cable conductor that functions as the one-wire data bus is connected to the contact pad that connects to the cannula NVRAM$_c$ 154. Internal to the control console 22 there is a NVRAM reader 164. The conductor internal of the plurality of conductors 115 forming the one-wire NVRAM data bus is connected to the NVRAM reader 164. The output data signals generated by NVRAM reader are supplied as input data to the microcontroller of the console 22. The analog signal generated by thermocouple 120 is applied to an analog to digital converter 168 also internal to control console 22. The digitized output signal from converter 168 is another input into the microcontroller 160.

FIGS. 21A and 21B collectively illustrate the types of data stored in either of the memories internal to NVRAMs 154 and 155. In a name field 170 there is data identifying the type of component. This information is presented on the display integral with the console I/O module 162. A part number field 172 contains part number data also presented on the console display. A revision field 174 contains data indicating the revision or form of the data stored in the NVRAM memory. These data are used by the microcontroller 160 to determine the types of the data in the subsequent memory fields. The serial number of the component with which the NVRAM is integral is stored in field 176. These data may be used to inhibit use of the component. This may be necessary if data received from another source informs the control console 22 that the particular component should not be used. Data in a manufacturer field 178 identifies the manufacturer of the component. These data are presented on the console display.

Data regarding the minimum software and hardware versions of the control console with which the component can be used are stored in fields 182 and 184, respectively. These data are used by the control console 22 to determine whether or not it has the minimum hardware and software to operate the component. Data in a GUI interface field 186 is used by the display controller to set the appropriate image on the control console display. A device type data field 188 contains information regarding the type of component. This information is presented on the display.

Some of the NVRAM data is specific to a particular component. For example, $NVRAM_c$ 154 integral with the cannula 28 contains a polarity field 189. The polarity field 189 contains data indicating the polarity (monopolar or bipolar) of the cannula 28. Field 190 contains data regarding whether or not the component is considered the primary or secondary component for regulating the operation of the system 20. Field 190 is thus referred to as the primary/secondary field. Field 191 is the partner field. The data in the partner field indicate what other components can be used with this component.

An operating mode field 192 contains data used to indicate the particular purpose for which the component is designed. For example, data in field 192 may be used to indicate if the component is designed to cut, coagulate or blend tissue. Control console 22 uses the data in operating mode field 192 to determine the characteristics of the console's electrical output.

Other data in the NVRAMs 154 and 155 describe the physical parameters of the components with which each NVRAM is integral. A gage field 194 contains data indicating the gage, the outer diameter of the component. For the cannula 28, this is the diameter across the outermost outer tube, tube 36 in FIG. 2. For the supply electrode assembly 36, this is the diameter across the electrode shell 122.

$NVRAM_c$ 154 integral with the cannula 28 also may contain a number of contacts field, field 196. This is because it is possible to provide an electrode with plural exposed conductive surfaces that simultaneously act as a common active contact. Number of contacts field 198 thus indicates the number of active contacts integral with the supply electrode or cannula 28. Field 202, the active contact length field, contains data indicating the longitudinal length of the distal most active contact, contact 62 of FIG. 14. A contact separation field, field 204, indicates the distance between the first active contact 62 and the second active contact 68.

Display length data field 204 contains data that indicates the overall length of the component. Thus, display length field 204, integral with cannula 28 contains data indicating the overall length of the cannula. Display length field 204 internal to a $NVRAM_E$ 155 integral with a supply electrode assembly 36 contains data indicating the overall length of the electrode shell 122. A physical characteristics field 208 contains data indicating certain data regarding the associated component that is not numerically quantified. These data, for example, are: whether or not the component is curved; or if the distal end tip of the component is blunt or other shape. Data in the physical characteristics field 208 of a cannula $NVRAM_c$ 154 also indicates if the most proximal end active tip has a non-circular shape and the nature of the shape, for example star shaped. Data in the physical characteristics field 208 of electrode $NVRAM_E$ 155 indicate the type of metal from which the electrode shell 122 is formed. The data in fields 188-208 are read by microcontroller 160 and presented on the console display.

Component NVRAMs 154 and 155 also contain data that regulate the operation of the component with which the NVRAM is integral. Some of these data are stored in feedback loop data field 210. These data include proportional integral derivative (PID) values that, as discussed below, regulates the operation of the system 20. Additional control data are stored in a crossover temperature field 212. These data are used to define a crossover temperature above and at or below which particular feedback loop constants are employed in the below discussed filtering algorithm. The NVRAM integral with a reusable component, i.e., the supply electrode assembly 36, contains an odometer set point field 214. The data in field 214 indicates the number of times the component can be used before it should be subjected to a maintenance overhaul. Field 214 may also contain data indicating the maximum overall number of times the component can be used.

Each NVRAM 154 and 155 also contains match data. The match data internal to the cannula $NVRAM_c$ 154 identifies the supply electrode assemblies 36 with which the cannula 28 can and cannot be used. The match data internal to the supply electrode $NVRAM_E$ 155 identifies the cannulae 28 with which the supply electrode assembly 36 can and cannot be used. As discussed below, there are two ways to match a cannula 28 and a supply electrode assembly 36, by part numbers or by characteristics. The match data stored in NVRAMs 154 and 155 is used to perform both types of matches.

These data include, in a part number field 218, a part number specific to the component with which the NVRAM 154 or 155 is integral, the cannula 28 or the supply electrode assembly 36, respectively. This part number identifies the component with regard to the below discussed matching registry. In some versions of the invention, data in part number field 218 is used to perform the below-discussed match process. This eliminates the need to provide a field 218 with identical data.

A match characteristics field 220 contains data that identifies the characteristics of the component for matching purposes. For a cannula 28, the data in field 130 indicates: if the cannula is monopolar or bipolar; the required length of the complementary electrode; if the cannula is a primary or secondary device; if the cannula requires a thermocouple in order to be operated; the temperature range of the thermocouple; the material that is acceptable for the complementary electrode; and the necessary gage of the complementary electrode. The data in the match characteristics field 220 in an electrode NVRAM$_E$ 155 is complementary to the above data. Specifically, the data in the field 220 of NVRAM$_E$ 155 includes: an indication regarding whether or not the electrode can be used with a monopolar or bipolar cannula; the length of the electrode; if the electrode is a primary or secondary device; if the electrode includes a thermocouple; the temperature range of the thermocouple; the material from which the electrode shell 122 is formed; and the gage of the electrode main body.

NVRAMs 154 and 155 also include a match table 222 and a lockout table 224. The data in the match table 222 identify, by part number, the components with which the component carrying the data can be used. The data in field 222 for the cannula NVRAM, 154 identifies the part numbers of the supply electrodes 36 with which the cannula can be used. The data in field 222 of electrode NVRAM$_E$ 155 identifies the part numbers of the cannulae 28 with which the supply electrode assembly 36 can clearly be used. The data in the lockout table 224 of each NVRAM 154 and 155 list the part numbers of the companion components with which the particular component clearly cannot be used.

Some NVRAMs 154 and 155 may also include one or more PID multiplier values. These data are stored in a PID multiplier field 226. The purpose for these data are discussed below.

NVRAMs 154 and 155 may also contain one or more memory fields in which data are written to by the control console 22 to which the associated component is attached. One of these fields is an odometer field 228. This field is present in the NVRAM of a component that is reusable, such as a reusable supply electrode 22. This field stores data indicating the number of times the particular component was used. In one version of the invention, odometer field is a multi-bit field. At manufacture or after complete overhaul, all bits are set to "0" or "1". Each time the component with a NVRAM including field 228 is plugged into the console. The state of the next unflipped bit is inverted.

VI. Operation

In operation, the cannula 28 and stylet 30 are supplied from the manufacturer preferably preassembled in the tissue penetration state 38 and in a sterile environment or package. Preferably with the guidance of X-ray or fluoroscopy, the cannula body 29 is inserted in the targeted nerve tissue. Once located, the stylet 30 is removed from the cannula 28 and discarded.

When connecting the supply electrode assembly 36, the distal end 123 of supply electrode 118 is first inserted through the rearward opened bore 72. The funnel portion 76 of the bore 72 acts to guide the distal end 123 to the small rearward opening of the through-bore 57 generally of cannula body 29. Once the supply electrode 118 begins insertion into the cannula body, the inner electrode 48 is in electrical contact with the outer wall 124 of the shell 122. This contact establishes a conductive link with the complementary power conductor in cable 114. The outer electrode 54 and associated terminal 86 has yet to make electrical contact with the terminal 140 of the coupling assembly 116 of the supply electrode assembly 36, hence, the circuit is not yet completed.

During insertion, the circumferential indexing feature 146 is properly aligned (i.e. tab 150 aligned to alcove 82). With continued insertion, the post 142 of the supply electrode assembly 36 begins to enter the blind bore 72 of the cannula 28. This substantially aligns the supply electrode 118 laterally to the through-bore 57 thus preventing potential damage and/ or plastic deformation of the supply electrode 118. Also, the forward projecting tab 150 begins to enter the alcove 82 assuring that the terminals 86, 140 are circumferentially aligned. Continued insertion causes the terminal 140 of the supply electrode assembly 36 to abut against contact pad 93 of the terminal 86 which in-turn causes the arm 88 of terminal 86 to flex or bow further within the alcove 82. This causes the spring or biasing force that presses the terminal end 90 against the outer tube 54 to increase providing a reliable electrical connection.

The axial alignment feature 148 carried between the hub 44 and the cartridge 138 prevents over insertion of the supply electrode 118 into the cannula 28 and assures that the distal end 123 and temperature sensor 120 of the supply electrode 118 are consistently located with respect to the cannula thus providing consistent and reliable operation of the system 20. More specifically, the distal end 123 of the supply electrode 118 is located at the distal end of the inner tube 48 of the cannula 28 when the rearward stop 104 carried by the hub 46 abuts the forward or leading stop 152 of the cartridge 138. Assuming cannula 28 and supply electrode assembly 36 are properly paired this means the distal end of the supply electrode shell 122 extends a short distance forward of the open end of cannula bore 57. For example, in versions of the invention wherein the distal end of the cannula inner tube 48 is beveled, the distal end of supply electrode shell 122 sits in the angular space defined by the beveled face of the cannula. This face in a cannula of 20 Gauge size may be in length between 0.065 and 0.090 inches.

With the electrode assembly 24 in the operating state 42, pain nerve stimulation is conducted (typically 50 Hz DC biphasic pulses) to ensure the RF energy is applied to the proper pain nerve. Next, motor nerve stimulation steps are then taken to ensure destructive energy is not applied to motor nerves. This process is typically performed by apply a signal at approximately 2 Hz. The signal applied at this point in the procedure is typically at a power level of 5 Watts or less.

After the nerve is located, it may be desirable to apply a therapeutic fluid or an anesthetic. If therapeutic fluids are needed after the penetration state 38, system 20 is placed into the medication state 40 by preferably press fitting a leading end of the syringe 32 against the collar 74 and into the bore 72 for slightly pressurized injection of the therapeutic fluid into the through-bore 57 of cannula body 29. After the medication state 40, the syringe 32 is preferably removed from the hub 46 and the supply electrode assembly 36 is connected thus designating the operation state 42 of the tool 24.

After the nerve is located and the option therapeutic (anesthetic) agent is applied, the nerve is subjected to the actual denervation procedure. The control console 22 generates the RF or Stimulation signal through the shell 122 of the supply electrode 118. The inner tube first active contact 62 functions as the active electrode and the second active contact 68 of the outer tube 54 functions as the return electrode. The RF signals emitted from the first active contact 62 flow through the tissue and return to the control console through the second active contact 68. A fraction of the energy in the RF signals is absorbed by the tissue. This RF energy is converted to thermal energy in order to cause the desirable therapeutic effect, the formation of a lesion; tissue ablation; or disruption of the cellular electrochemical structure.

Upon completion of the denervation procedure, cannula 28 is preferably discarded and the supply electrode assembly 36 is sterilized and preserved for reuse.

It should be appreciated that the bipolar version of this invention means that the need to use the ground pad of a monopolar assembly is eliminated. The elimination of the ground pad means can, for some procedures, reduce complexity. Further the cost associated with providing the ground pad is eliminated.

It should also be appreciated that the cannula 28 and electrode assembly 36 is preferably used in conjunction with the control console 22 to create radio frequency (RF) lesions in nerve tissue. The control console 22 applies temperature-controlled, RF energy into targeted nerve tissue via the supply electrode 118. This energy destroys the nerve tissue's ability to conduct electrical signals. Pain relief is achieved by creating defined lesions on pain-conducting nerve fibers or tissue. The system may also be used in "pulsed mode." Instead of creating heat lesions, RF energy is pulsed with a duty cycle low enough that tissue temperature rise is kept below a level which can kill cells. Pain relief is achieved by influencing the nerve tissue through the pulsed E field. It is theorized that the intense E field created by the pulsed RF influences gene expression in the nerves. This changed gene expression provides a pain reduction.

Operation of the system 20 with regards to NVRAMs 154, 155 is now described wherein the control console 22 is initially actuated. Initially, the control console 22 is actuated as represented by step 250. While not illustrated, it should be understood that, as part of the initialization step 250, microcontroller 160 performs a self-test on the other components of the control console 22. If the self-test detects a fault state, appropriate data are presented on the I/O module 162.

Microcontroller 160, in step 252, then causes the I/O module 162 to present an image inviting the surgical personnel to identify if a specific doctor and/or specific procedure is going to be performed. If, in step 254, such data are entered, microcontroller 160 retrieves from the console memory any stored data specific to the doctor and/or procedure, step 256e. These data, for example, may include initial and/or maximum temperature settings preferred by the doctor. Additional doctor or procedure preference data includes duration of treatment, waveform optimization, or electrical stimulation data. These data are then used later to control the operation of the system 20.

The next step in the operation of the system, step 258, is the attachment of the supply electrode 36. This is performed by the coupling of the electrode coupling assembly 116 to cable 114.

Once the supply electrode assembly 36 is attached, the data in the electrode $NVRAM_E$ 155 are read, step 260. As is known in the art, once the control console 22 is initialized, microcontroller 160 periodically instructs the NVRAM reader 164 to send out interrogation signals. As long as no components are attached to cable 114, no response to these signals are received. Once a supply electrode assembly 36 is attached, the electrode $NVRAM_E$ 155 sends out a brief acknowledgement to the basic interrogation. When this response is received, NVRAM reader 164, in turn, reads out all of the data in the $NVRAM_E$ 155. These data are then forwarded to microcontroller 160.

Microcontroller 160 then, in step 262, determines if the supply electrode assembly 36 is on a basic lockout list and should not be used. As part of the lockout testing, microcontroller determines, by reference to data in the minimum software and hardware revision fields 178 and 184, respectively, if the control console has the minimum software and hardware to actuate the electrode. As part of step 262, microcontroller 160 also determines if the serial number of the electrode from field 176 is in a table of lockout components. This table is stored in the control console memory 161. The data in the table are updated by a network connection to the control console 22 or an update to the system software. Thus, in the event the manufacturer determines there is a reason not to use a specific lot of manufactured components, the serial number data for the components are forwarded over the network connection to the control console 22 and stored in the component lockout table internal to memory 161.

If, in step 262, it is determined the attached electrode should not be used, microcontroller 160 causes an appropriate warning message to be presented on the I/O module 162, step 264. Surgical personnel should then remove the attached electrode (step not shown). A new supply electrode assembly 36 is attached; step 258 is reexecuted.

If in, step 262, it is determined the electrode 22 is available for use, microcontroller 160, in step 266, displays on the I/O module 162 data that describes the characteristics of the electrode. These data are the data read from the name, part number and physical characteristics fields 170, 172, 192, 194, 196, 198, 202 and 204 of the $NVRAM_E$ 155.

In a step 268, the microcontroller 160 also causes to be presented on the display of the I/O module 262 information regarding suitable cannulae 28 that can be matched with the supply electrode assembly 36. These information include part numbers of acceptable cannulae based on the data in the match table 222 from $NVRAM_E$ 155. The information also includes the characteristics of specific matchable cannulae. These data are the data contained in the match characteristics field 220 of $NVRAM_E$ 155

Based on the match data presented on the I/O module 162, the surgical personnel, in step 270, select an appropriate cannula 28 and attach it to the system 20. The selected cannula is fitted over the electrode main body 46 so that the cannula hub 46 couples to the electrode coupling assembly 116. Then, in step 272, the data in the cannula $NVRAM_C$ 154 are read. The reading of the data in the cannula $NVRAM_C$ 154 occurs because, even though, the supply electrode assembly 36 and $NVRAM_E$ 155 are attached to the control console 22, the NVRAM reader 164 continues to send out basic interrogation signals. Once the data in the electrode $NVRAM_E$ 155 are read, $NVRAM_E$ 155 is instructed to periodically not to respond to a basic interrogation signal. During the time periods in which $NVRAM_E$ 155 is silent, NVRAMc 154 responds to the basic interrogation signal. Once the basic response is received, NVRAM reader 164 reads the data in $NVRAM_C$ 154.

Once the data in $NVRAM_C$ 154 are read, microcontroller 160 determines if the cannula 24 meets minimum use criteria for the rest of the system 20, step 174. In step 274, which is similar to step 262, a basic determination is made regarding if it is appropriate to use the cannula 24 with the control console 22. These determinations are based on the cannula minimum software and hardware revision requirements and the cannula serial or lot number.

Also as part of step 274, the data in the cannula odometer field 228 is checked. If the data in this field and in the limits field 124 indicate the cannula 26 is overdue for major maintenance or was used for more than its useful cycles, microprocessor 60 considers the cannula unusable or displays a warning message to the user.

If, as a result of the evaluation performed in step 274, it is determined that the cannula is not appropriate for the rest of the system, in step 276, a warning message is presented on the I/O module. In step 276, a message concerning the problems with the cannula is presented. The surgical personnel then remove the cannula, step not shown, and a new cannula is selected and attached, step 270 is reexecuted.

Once the fundamental determination has been made that it is appropriate to use the cannula 24 with control console 22, the actual matching process starts. This process starts with the basic part number match determination, step 278. In this step, the microcontroller 160 determines if the part number for the cannula, from NVRAM$_C$ 154 part number field 218, is on the table of part numbers from the match table 132 for the supply electrode 36. If this determination is positive, microcontroller 160 continues to configure the system for operation, step 284.

If the determination in step 278 is negative, microcontroller 160 proceeds to a part number lockout determination, step 280. In step 280, microcontroller 160 determines if the cannula part number is on the lockout table 224 for the attached supply electrode assembly 36. If this determination is positive, microcontroller 160 executes step 276. During this execution of step 276, microcontroller 160 causes an appropriate message to be presented on the I/O module 162 explaining why the cannula 28 is unsuitable for use.

If in step 280, it is determined that the cannula 28 can potentially be used with the supply electrode assembly 36, a characteristics match step 282 is performed. In step 182, microcontroller 160 determines if the characteristics of the cannula 28 indicate that it can be used with the supply electrode assembly 36. Step 282 is performed by comparing the data from the match characteristics field 130 of the cannula NVRAM$_C$ 154 to the data from the match characteristics field 130 for the supply electrode NVRAM$_E$ 155. This determination will indicate that the cannula 28 and supply electrode assembly 36 are compatible if: the cannula and electrode are both intended for monopolar or bipolar use; if the electrode is of an appropriate length and gage for the cannula; the electrode has the appropriate thermocouple 48; and the material from which the electrode main body is formed is appropriate for the cannula. If, in step 282 it is determined that the components are appropriate for each other, microcontroller 160 proceeds to the configure system step 184.

Alternatively, if in step 282 it is determined that the components are not appropriate for each other, step 276 is executed an appropriate message is presented on the I/O module 162.

In step 284, microprocessor 60 configures the system 20 of this invention for operation based on the operational data contained in NVRAMs 154 and 155. This includes presenting information on the I/O module 162 that represents the attached cannula 28 and supply electrode assembly 36 sub-assembly.

Microcontroller 160, as part of step 284, establishes initial and maximum operating temperatures for the cannula 28 and supply electrode assembly 36 sub-assembly and/or establishes the temperature profile. Power levels and frequency for the signals that are generated by RF generator 56 may also be set. Stimulation Values may also be set. These operating parameters may be established based on data in one of the NVRAMs 154 or 155 or based on data in a lookup table in the console memory 61. If a doctor and/or procedure identifying information was loaded in step 156, then these parameters are established based on this retrieved information.

Figure 23:
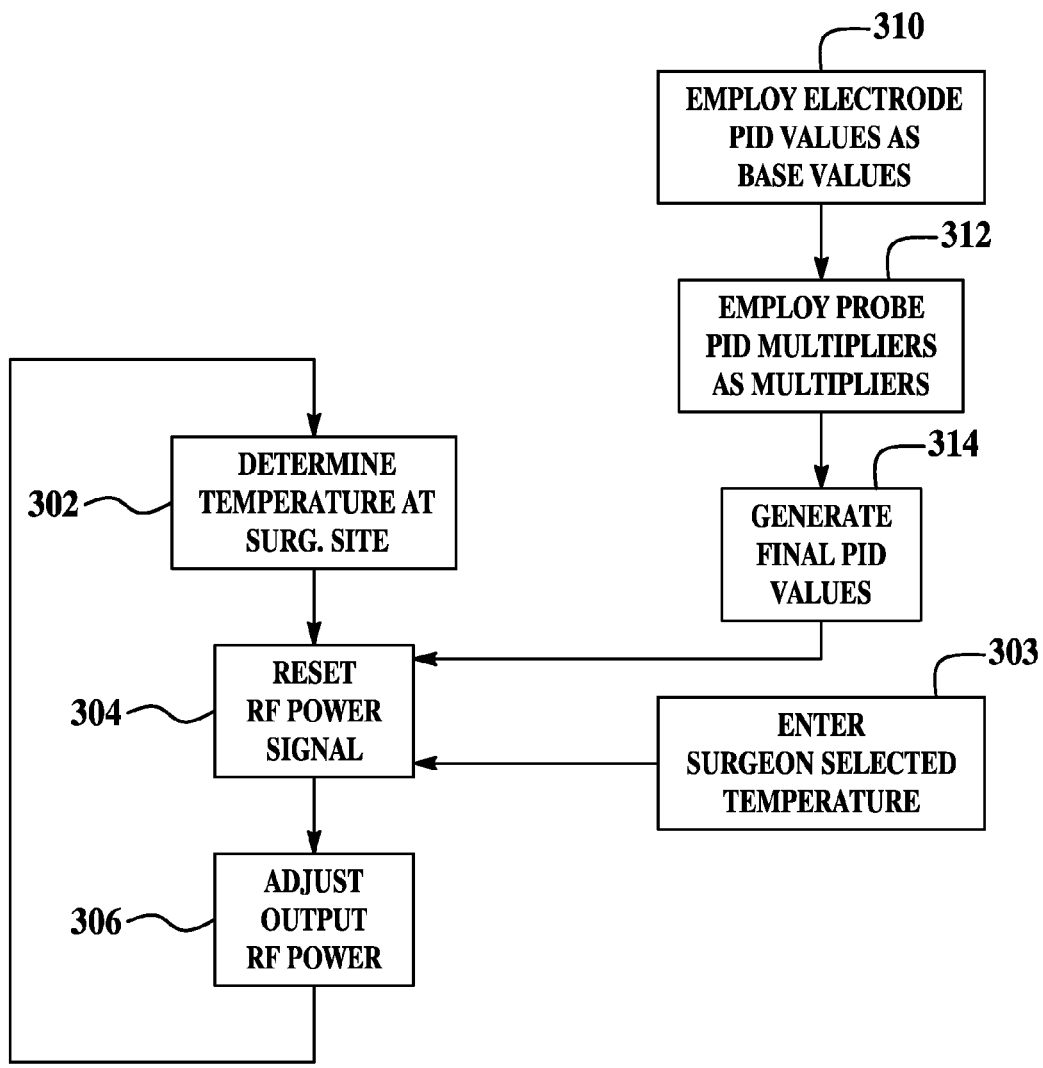
FIG. 23 is a flow diagram illustrating the process steps by which a PID value is generated and how the PID value is employed to regulate the power generated by the system.

As part of step 284, microcontroller 160 also configures the control algorithm for operation. As illustrated in FIG. 23, this algorithm provides closed-loop control of the generation of power by the system 20. Initially, in step 302, as part of this process, the temperature at the surgical site is measured and supplied to the microcontroller 160. Specifically, the analog signal from thermocouple 120 is applied to the console A/D converter 168. Converter 168 generates a digitized version of the signal. The digitized temperature is forwarded to the microcontroller 160. Not shown are the steps of correcting and filtering of the temperature signal. Temperature correction may be performed using an algorithm wherein the correction variables are data retrieved from the electrode NVRAM$_E$ 155 (fields not shown). The correction variables are employed as constants in a mono-, bi- or tri-nominal equation specific to the thermocouple 120. This correction process is performed to eliminate any variations in output signals based on the manufacturing variations of the thermocouples. Filtering is performed on the temperature signal to eliminate the effects of any spikes. Variables to regulate the filtering, which may be either infinite impulse response or finite infinite response filtering, may also be supplied by the electrode NVRAM$_E$ 155.

The corrected and filtered temperature signal is then used in a reset power step 304 to determine the extent to which the power level of the signal output by the RF generator 156 should be reset. In step 304, microcontroller 160 employs a proportional integral derivative algorithm to determine the extent to which the RF generator output signal should be reset. The two inputs into this algorithm are the corrected and filtered temperature signal from thermocouple 48 and the surgeon selected operating temperature for the cannula 28 and supply electrode assembly 36 subassembly. In FIG. 5, this temperature is shown as being entered through step 304. It should be appreciated that step 303 is performed when the system 20 is first actuated and is reexecuted as necessary by the surgeon. Again, the temperature profile for step 304 may come from the preference data loaded in step 256.

Based on the difference between the two temperatures and the below-discussed derivative variables, in step 306, microcontroller 160 resets the signal indicating how much power the RF generator 56 should output. The RF generator 56, in step 208, based on the reset power level signal, readjusts the power of the signal supplied to the cannula 28 and supply electrode assembly 36 subassembly. Steps 302, 306 and 308 are then continually reexecuted in order to ensure that the system 20 heats the tissue to which the cannula 28 is applied to the appropriate temperature.

As mentioned above, in step 304, the proportional integral derivate algorithm is employed to determine, based on the difference between the measured, corrected and filtered temperature signal and the surgeon-selected signal, the extent to which the RF power signal should be adjusted. The proportional, integration and derivative constants for the algorithm come from the PID data in the NVRAMs 154 and 155. Specifically, as part of the system configuration, step 304, in a step 310, microcontroller 160 employs the PID values from the feedback loop data field 210 of the electrode NVRAM$_E$ 155 as the "base" PID values, step 190. In step 312, the PID multiplier values extracted from the PID multiplier field 216 of the cannula NVRAM$_C$ 154 are selected as multipliers. In step 314 the base PID values are multiplied by the multiplier values. The resultant products are the final PID values. These are the PID values employed in step 306 by the PID algorithm to determine the extent to which the RF power signal should be reset. The PID values may also come directly from the values contained in NVRAM$_C$ 154.

The electrosurgical tool system 20 of this invention is designed so that once an supply electrode assembly 36 is coupled to the control console 22, the surgical personnel are presented with information that identifies the cannulae 22 that can be used with the electrode. Once a cannula 28 is attached to the supply electrode assembly 36, microcontroller 160 determines if the cannula is appropriate.

Initially, this determination of cannula appropriateness is made by determining if the part number for the cannula is on tables that list acceptable and unacceptable cannulae. This provides a quick initial determination of whether or not the selected cannula is appropriate. Only if this evaluation does not reveal the appropriateness of the cannula 28, is a more detailed evaluation of appropriateness based on matching the characteristics of the cannula to those of the electrode executed. If this evaluation reveals that the cannula 28 is not an appropriate match for the supply electrode assembly 36, the surgical personnel are presented with notice of this fact. Thus, system 20 both provides surgical personnel with a list of cannulae that can be attached to the electrode so as to reduce the time needed to make this determination and eliminates the possibility that surgical personnel could unknowingly attach a cannula that is inappropriate for the electrode.

Once a cannula 28 and supply electrode assembly 36 are coupled to the control console 22, microprocessor 160 generates PID values for the control algorithm used to regulate the power output by the RF generator 156. These values are based on the PID values and PID multiplier values specific to the attached cannula and electrode. Thus, the values may be specific to the attached cannula and electrode so as to compensate for manufacturing differences of the individual components. Since the PID values are generated automatically based on data read from the component NVRAMs 154 and 155, the possibility that human error can result in incorrect values being input to the control algorithm is essentially eliminated.

It should be recognized that the above description is directed to one specific version of system 20 of this invention. Alternative versions of the system may be possible. For example, in the described version of the system, the attached supply electrode assembly 36 is considered the "secondary" component. This is because once the supply electrode assembly 36 is coupled to the control console 22, it is necessary to attach a cannula 28 with characteristics that match the electrode. Thus, the cannula 24 is the "primary" component.

In an alternative construction of system 20, the primary/secondary roles of the components are reversed. This is accomplished, for example by providing the cannula 28 with a radio frequency identification device (RFID) 320. In FIG. 20, RFID chip 320 is shown mounted in the cannula hub 46. This is exemplary. In some versions of the invention, RFID 320 may be mounted in the package in which the cannula 28 is shipped. The RFID 320 contains data substantially identical to the data contained in the NVRAM$_c$ 154. At the start of the procedure, the data in the RFID are read. In FIG. 20 control console 22 is shown to have an RFID reader 322 able to perform this function. Again, this is exemplary. The RFID reader may be attached to pointer in the operating room used to read RFID 3200 as well as RFIDs integral with other devices and components used in the procedure. The data from RFID 320 is forwarded from the reader 212 to the console microcontroller 160.

Figure 22A:
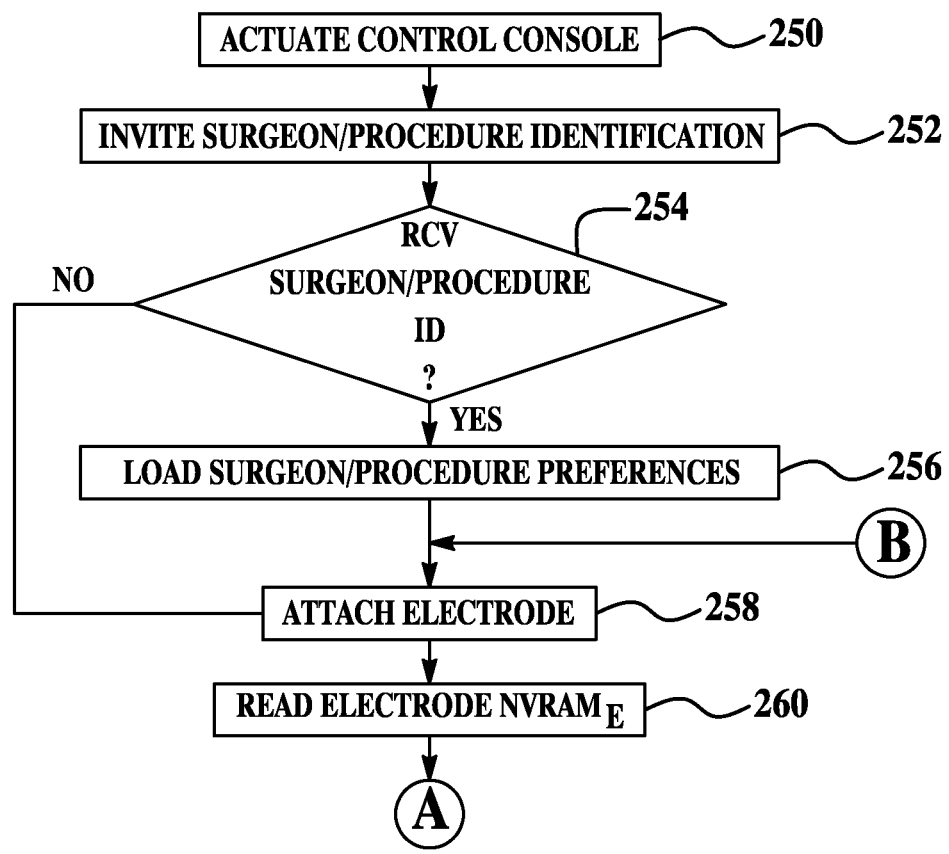
FIGS. 22A-22C collectively form a flow diagram of the process steps executed to actuate the electrosurgical tool system.
Figure 22B:
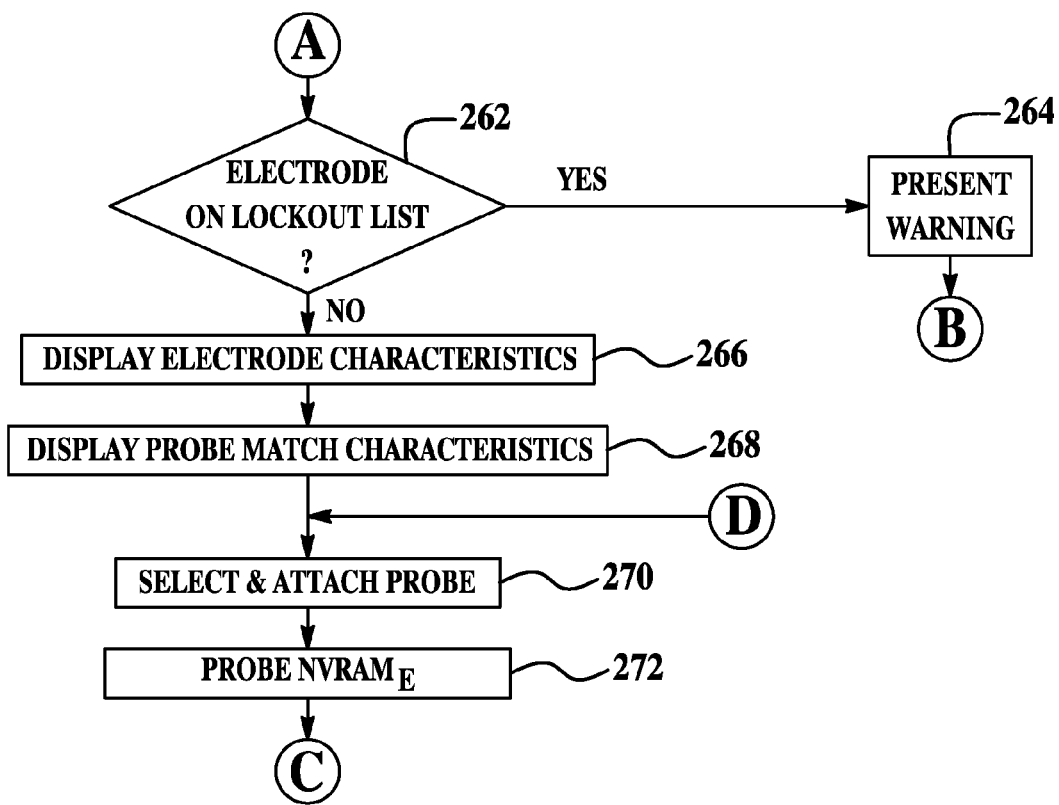
Figure 22C:
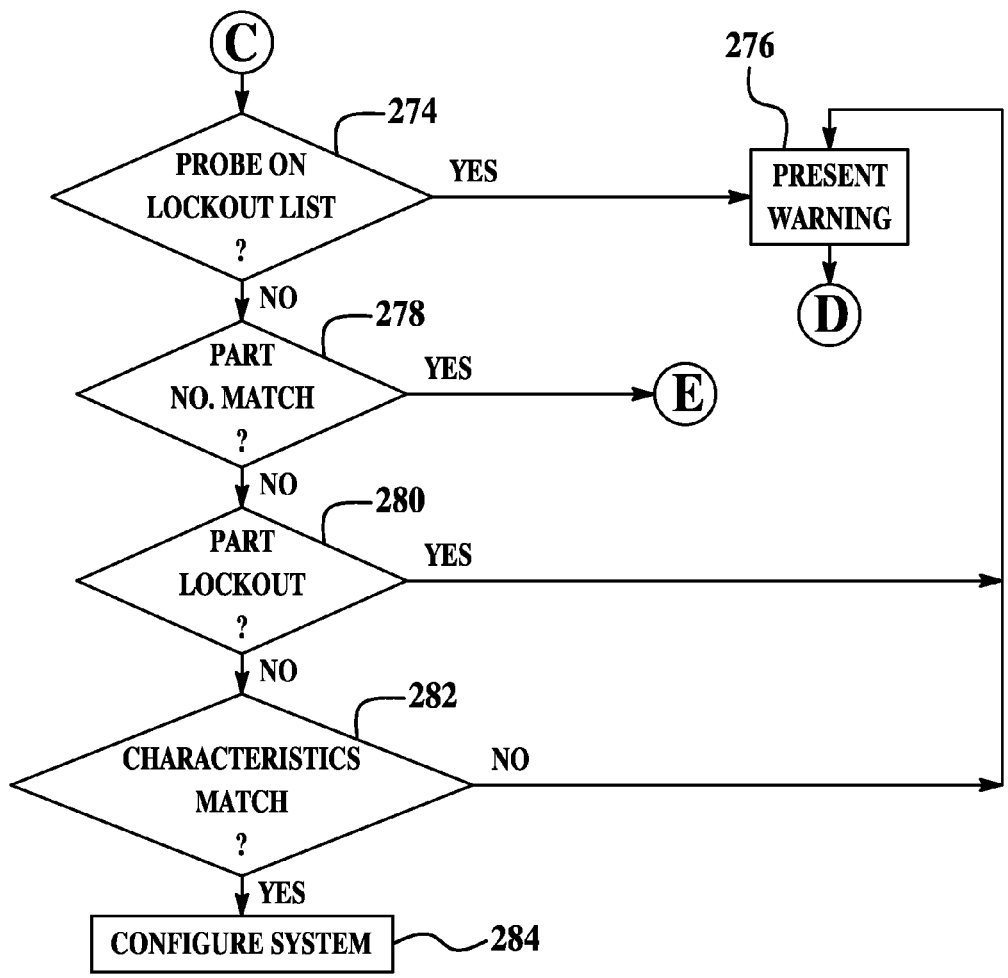

Based on the data in the cannula RFID 320, microcontroller 160 generates a list of electrodes that are appropriate for use with the cannula 28. Once a supply electrode assembly 36 is attached, microcontroller 160 engages in a process similar to that described with reference to FIGS. 22B-22C to determine if the selected supply electrode assembly 36 is appropriate.

VII. Monopolar Electrode Assembly

A monopolar electrode assembly of this invention is constructed out of components similar to the above described components. Specifically, there is a cannula that comprises the inner tube 48 with active tip 62 and insulating sleeve 52. Hub 56 is attached to the proximal end of tube 48. End 90 of terminal 86 abuts an exposed proximal end surface of inner tube 48.

Monopolar electrode assembly of this invention includes a head unit visually similar to the supply electrode assembly. However, in this version of the invention, shell 122 is not conductive. Instead, shell 122 serves as an insulating housing for ensuring that the temperature transducer 120 is properly positioned relative to active contact 62. Thus shell 122 is a non-conductive post. Coupling assembly 116 is also part of this head unit.

A conventional ground pad is used as the return electrode for the monopolar version of this invention.

In this version of the invention, the electrical path between active tip 62 and the control console is established by connecting the head unit to the monopolar cannula. This coupling results in the proper position of the temperature transducer 120 to the active contact 62. This coupling also results in the electrical connection of active tip 62 to the control console through a conductor in cable 114. contact 140 of the head unit and terminal 86 of the cannula assembly.

The above described arrangement thus means that the monopolar electrode assembly of this invention is constructed so that the need to provide the head unit, which is reusable, with a shell that is conductive is eliminated. This serves to minimize the costs associated with making this assembly in comparison to those associated with providing reusable supply electrodes wherein the associated shell is conductive.

With regards to NVRAMs utilized with the monopolar electrode assembly, a memory such as the NVRAM 340 is fitted in the ground pad proximal end plug (FIG. 20). The memory contains data that indicates the characteristics of the ground pad. The memory integral with monopolar cannula contains data that describes the characteristics of the ground pads that can be used with the cannula. These data identify acceptable ground pads both by part number and physical characteristics. The data include for example, the minimum and maximum surface areas of the conductive portion of the ground pad and split versus solid construction.

As part of the configuration of the system for operation, the microcontroller previously described of the control console 22 receives from the ground pad memory data that describes the ground pad. For example, the plugging in of the ground pad to the console 22 connects a ground pad NVRAM$_{GP}$ to the NVRAM reader of the console 22. Microcontroller then performs an evaluation similar to that previously described in "VI Operation" section except to determine if the ground pad is appropriate for the cannula. As part of this evaluation, the characteristics of the supply electrode coupled to the cannula may be used as input variables. This process essentially eliminates the possibility that system 20 can be configured for monopolar operation with a cannula and ground pad that are inappropriately matched.

VIII. Alternative Embodiments

Alternative versions of the invention are possible. For instance, the electrically conductive outer tube 54 may also be an elongated member having a circumferentially non-continuous strip (not shown) that carries the proximal end that is in electrical contact with terminal 86. From the proximal end, the strip extends axially forward to the second active contact 68 of the elongated member 54. Preferably, the contact 68 is ring-shaped and thus circumferentially continuous with respect to axis 50 for energy flux distribution in the tissue.

Further, the memories employed in the cannula 28 and supply electrode assembly 36 of system 20 may be different than the described NVRAMs and RFID. There may be versions of the invention in which the appropriate memory integral with electrode is an RFID. Still other memory devices, such as optically read memories may be employed. These memory devices include bar codes. In some versions of the invention, one or more precision resistors or mechanical keying may function as the memory for the cannula and/or supply electrode.

Moreover, there is no requirement that in all versions of the invention, the match data that identifies an appropriate secondary component is solely data read from the memory from the primary component. In some versions of the invention, match data may be stored in look-up tables within the console memory 161. In these versions of the invention, the only "match" data stored in the memory of the primary component is the part number of the primary component. Based on this information, microcontroller 160 retrieves from memory 161 data that describe the match characteristics of a component that can be coupled to the primary component. These data include: lists of part numbers of secondary components that can and cannot be mated with the primary component; and a list of acceptable characteristics of the secondary component.

Furthermore, there is no requirement that in all versions of the invention, that the PID values be generated exactly as described. In some versions of the invention, it may not be necessary to adjust the PID values retrieved from the electrode $NVRAM_E$ 155 by multipliers from the cannula NVRAM, 154. Also, in some versions of the invention, the PID values retrieved from the cannula NVRAM alone serve as the PID values used to regulate power. Data fields in the cannula and supply electrode NVRAMs indicate if the PID values in the NVRAM are primary values, values that in most instances are used, or secondary values, values that in certain predefined circumstances are substituted for the primary values. Alternatively, the NVRAM data may indicate the PID values are multipliers, PID values that are multiplied with the PID values from the other component to obtain the final PID values.

The sequence of processes executed by the microcontroller to match components and configure the system is likewise only exemplary, not limiting. Also, there is no requirement that, if it is determined that a cannula 28 or supply electrode assembly 36 are unsuitable for use, control console 22 actually prevent the use of the component(s). Thus, after a determination of unsuitability is made, control console 22 may merely present this information on the I/O module display. The surgeon would then be required to acknowledge the determination and, then, the control console 22 will energize the cannula 28 and supply electrode assembly 36.

In still other versions of the invention, the components that supply the base PID values and the PID multiplier values are different from the above described versions of the invention. Thus, the data in NVRAMs 154, 155, may indicate that, for a particular cannula 28 and supply electrode 118, the cannula supplies the base PID values and the electrode the PID multiplier values. Hence, the microcontroller first reads the data in the cannula and electrode memories to determine which of the two components supplies the base PID values and which one supplies the PID multiplier values. Based on this determination, data from the appropriate fields internal to NVRAMs 154, 155 are read and multiplied to establish the PID values supplied to the control algorithm. The multiplier may also be used to adjust system performance without the need to reprogram the console.

There has been shown and described a unique design and concept of an electrosurgical tool system. While this description is directed to a few particular embodiments, it is understood that those skilled in the art may conceive of modifications and/or variations to the specific embodiments shown and described herein. Any such modifications or variations which fall within the purview of this description are intended to be included herein as well. It is understood that the description herein is intended to be illustrative only and is not intended to be limited.

What is claimed is:

1. An electrode assembly comprising:
   a cannula having:
      a first coupling assembly with a hub; and
      an elongated tubular body having a proximal end mounted to said hub of said first coupling assembly and projecting outward to a distal end, first and second spaced apart active contacts disposed adjacent to said distal end, and a first conductive terminal seated in said hub and electrically connected to said second active contact; and
   a supply electrode assembly having:
      a supply electrode having a proximal end spaced apart from a distal end, said supply electrode defining a longitudinal axis;
      a second coupling assembly attached to said proximal end of said supply electrode; and
      a second conductive terminal attached to said second coupling assembly;
   said supply electrode is dimensioned to be slidably inserted in said elongated tubular body so as to be positioned to electrically contact said first active contact;
   said first and second coupling assemblies are configured to releasably interlock such that relative rotational movement between said first and second coupling assemblies is constrained to prevent clockwise and counterclockwise rotation of said supply electrode in said elongated tubular body with respect to said longitudinal axis; and
   said first and second conductive terminals are collectively positioned so that when said first and second coupling assemblies releasably interlock, said first and second conductive terminals contact each other.

2. The electrode assembly set forth in claim 1 wherein said elongated tubular body includes an inner tube having said first active contact with a through-bore defined by and extending co-axially with said inner tube.

3. The electrode assembly set forth in claim 2 wherein said supply electrode is disposed at least in-part in said through-bore.

4. The electrode assembly set forth in claim 2 further comprising an outer cylindrical shell of said supply electrode being in electrical contact with an inner cylindrical wall of said inner tube.

5. The electrode assembly set forth in claim 4 wherein a clearance between said outer cylindrical shell and said inner cylindrical wall is less than 0.025 mm.

6. The electrode assembly set forth in claim 2 wherein said through-bore communicates through said distal end of said elongated tubular body.

7. The electrode assembly set forth in claim 1 wherein said distal end of said supply electrode is generally axially aligned to said distal end of said elongated tubular body when said first and second coupling assemblies are releasably interlocked.

8. The electrode assembly set forth in claim 1 further comprising a temperature sensor disposed in said supply electrode near said distal end of said supply electrode for measuring tissue temperature.

9. The electrode assembly set forth in claim 7 further comprising first and second stops carried by said first and second coupling assemblies for maintaining consistent axial alignment of said distal end of said supply electrode with said distal end of said elongated tubular body.

10. The electrode assembly set forth in claim 1 wherein said supply electrode is formed from a nickel titanium alloy.

11. The electrode assembly set forth in claim 1 wherein said first coupling assembly includes an alcove formed in said hub and wherein said second coupling assembly includes a housing from which said supply electrode extends and a tab that extends from said housing, said tab dimensioned to sit in said alcove.

12. The electrode assembly set forth in claim 11 wherein said first conductive terminal is seated in said alcove and wherein said second conductive terminal is mounted in said housing so that when said tab is disposed in said alcove, said second conductive terminal abuts said first conductive terminal.

13. The electrode assembly set forth in claim 1 wherein said cannula includes a memory that contains data describing characteristics of said cannula and wherein said supply electrode assembly includes a contactor positioned to mate with said memory when said first and second coupling assemblies releasably interlock.

14. An electrode assembly comprising:
a cannula having:
a first coupling assembly having a first circumferential indexing feature; and
an elongated tubular body having a proximal end mounted to said first coupling assembly and projecting outward to a distal end, first and second spaced apart active contacts disposed adjacent to said distal end, and a first conductive terminal seated in said first coupling assembly and electrically connected to said second active contact; and
a supply electrode assembly having:
a supply electrode having a proximal end spaced apart from a distal end, said supply electrode defining a longitudinal axis;
a second coupling assembly attached to said proximal end of said supply electrode and having a second circumferential indexing feature; and
a second conductive terminal attached to said second coupling assembly;
said supply electrode is dimensioned to be slidably inserted in said elongated tubular body so as to be positioned to electrically contact said first active contact; and
said first and second coupling assemblies are configured to releasably interlock thereby constraining relative rotational movement between said first and second coupling assemblies to prevent clockwise and counterclockwise rotation of said supply electrode in said elongated tubular body with respect to said longitudinal axis when said first and second circumferential indexing features mate.

15. The electrode assembly set forth in claim 14 wherein said elongated tubular body includes an inner tube having said first active contact with a through-bore defined by and extending co-axially with said inner tube.

16. The electrode assembly set forth in claim 15 further comprising an outer cylindrical shell of said supply electrode being in electrical contact with an inner cylindrical wall of said inner tube.

17. The electrode assembly set forth in claim 16 wherein a clearance between said outer cylindrical shell and said inner cylindrical wall is less than 0.025 mm.

18. The electrode assembly set forth in claim 14 further comprising a temperature sensor disposed in said supply electrode near said distal end of said supply electrode for measuring tissue temperature.

19. An electrode assembly comprising:
a cannula having:
a first coupling assembly with a hub; and
an elongated tubular body having a proximal end mounted to said hub of said first coupling assembly and projecting outward to a distal end, first and second spaced apart active contacts disposed adjacent to said distal end, and a first conductive terminal seated in said hub and electrically connected to said second active contact; and
a supply electrode assembly having:
a supply electrode having a proximal end spaced apart from a distal end, said supply electrode defining a longitudinal axis;
a temperature sensor disposed near said distal end of said supply electrode;
a second coupling assembly attached to said proximal end of said supply electrode; and
a second conductive terminal spaced from said supply electrode and attached to said second coupling assembly;
said elongated tubular body defines a through-bore dimensioned to receive said supply electrode so that said supply electrode is positioned to electrically contact said first active contact and said temperature sensor is positioned to measure tissue temperature; and
said first and second coupling assemblies are configured to releasably interlock such that relative rotational movement between said first and second coupling assemblies is constrained to prevent clockwise and counterclockwise rotation of said supply electrode in said elongated tubular body with respect to said longitudinal axis.

* * * * *